US 7,097,853 B1

(12) United States Patent
Garbe et al.

(10) Patent No.: US 7,097,853 B1
(45) Date of Patent: Aug. 29, 2006

(54) MATRIX FOR TRANSDERMAL DRUG DELIVERY

(75) Inventors: James E. Garbe, Inver Grove Heights, MN (US); Daniel C. Duan, St. Paul, MN (US); Cheryl L. Moore, Afton, MN (US); Jamieson C. Keister, Lakeville, MN (US); Chan U. Ko, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1826 days.

(21) Appl. No.: 08/968,519

(22) Filed: Nov. 12, 1997

Related U.S. Application Data

(63) Continuation of application No. 08/523,762, filed on Sep. 5, 1995, now abandoned, which is a continuation-in-part of application No. 08/305,833, filed on Sep. 14, 1994, now abandoned.

(51) Int. Cl.
*A61M 37/00* (2006.01)

(52) U.S. Cl. ...................... 424/449; 424/448
(58) Field of Classification Search ................ 526/328, 526/328.5, 329.2, 329.7; 525/301, 308, 309, 525/303; 524/560, 561; 424/448, 449; 428/447, 428/483
See application file for complete search history.

(56) References Cited

U.S. PATENT DOCUMENTS

| | | | |
|---|---|---|---|
| RE24,906 E | 12/1960 | Ulrich | 206/59 |
| 3,786,116 A | 1/1974 | Milkovich et al. | 260/885 |
| 3,832,423 A | 8/1974 | Milkovich et al. | 260/878 |
| 3,842,057 A | 10/1974 | Milkovich et al. | 260/93.5 |
| 3,842,058 A | 10/1974 | Milkovich et al. | 260/93.5 |
| 3,842,059 A | 10/1974 | Milkovich et al. | 260/93.5 |
| 3,842,146 A | 10/1974 | Milkovich et al. | 260/879 |
| 3,862,077 A | 1/1975 | Schulz et al. | 260/29.6 |
| 3,862,098 A | 1/1975 | Milkovich et al. | 260/93.5 |
| 3,862,101 A | 1/1975 | Milkovich et al. | 260/94.7 |
| 3,862,102 A | 1/1975 | Milkovich et al. | 260/94.7 |
| 3,879,494 A | 4/1975 | Milkovich et al. | 260/876 |
| 3,928,255 A | 12/1975 | Milkovich et al. | 260/2.5 |
| 3,989,768 A | 11/1976 | Milkovich et al. | 260/859 |
| 4,085,168 A | 4/1978 | Milkovich et al. | 260/886 |
| 4,260,659 A | 4/1981 | Gobran | 428/217 |
| 4,304,591 A | 12/1981 | Mueller et al. | 71/93 |
| 4,374,883 A | 2/1983 | Winslow | 428/40 |
| 4,551,388 A | 11/1985 | Schlademan | 428/355 |
| 4,554,324 A | 11/1985 | Husman et al. | 525/301 |
| 4,656,213 A | 4/1987 | Schlademan | 524/272 |
| 4,693,776 A | 9/1987 | Krampe et al. | 156/327 |
| 4,732,808 A * | 3/1988 | Krampe | 428/355 |
| 4,737,559 A | 4/1988 | Kellen et al. | 526/291 |
| 4,751,087 A * | 6/1988 | Wick | 424/449 |
| 4,818,540 A | 4/1989 | Chien et al. | 424/448 |
| 4,847,137 A | 7/1989 | Kellen et al. | 428/195 |
| 4,851,278 A | 7/1989 | Enanoza | 428/195 |
| 4,871,812 A | 10/1989 | Locast et al. | 525/186 |
| 4,883,669 A | 11/1989 | Chien et al. | 424/448 |
| 4,906,169 A | 3/1990 | Chien et al. | 424/448 |
| 4,946,742 A | 8/1990 | Landin | 428/354 |
| 4,973,468 A | 11/1990 | Chiang et al. | 424/449 |
| 4,994,267 A | 2/1991 | Sablotsky | 424/78 |
| 4,994,322 A | 2/1991 | Delgado et al. | 428/343 |
| 5,006,582 A | 4/1991 | Manicinelli | 524/271 |
| 5,023,084 A | 6/1991 | Chien et al. | 424/448 |
| 5,032,637 A | 7/1991 | Therriault et al. | 524/375 |
| 5,053,227 A | 10/1991 | Chiang et al. | 424/448 |
| 5,059,426 A | 10/1991 | Chiang et al. | 424/449 |
| 5,143,972 A | 9/1992 | Groves | 525/71 |

(Continued)

FOREIGN PATENT DOCUMENTS

| | | |
|---|---|---|
| EP | 0183386 | 6/1986 |
| EP | 0353677 | 2/1990 |
| EP | 399432 A2 | 11/1990 |
| EP | 455458 A2 | 11/1991 |
| EP | 0491169 | 6/1992 |
| EP | 0501124 | 9/1992 |
| EP | 554106 A1 | 8/1993 |
| EP | 732100 A2 | 9/1996 |
| JP | 57-125753 | 8/1982 |
| JP | 58-176208 | 10/1983 |
| JP | 60-228413 | 11/1985 |
| JP | 01-213379 | 8/1989 |
| WO | 93/06184 | 4/1993 |
| WO | 94/13750 | 6/1994 |

OTHER PUBLICATIONS

Chemical Abstracts, vol. 96, No. 20 (May 17, 1982); Abstract No. 168739 (Japanese Patent No. 57-011916).
*Textbook of Polymer Science*, Wiley Interscience, pp. 84 and 85, 1971.
Pfister et al., "Developing Drug–Compatible Adhesives for Transdermal Drug Delivery Devices." *Pharmaceutical Technology*, pp. 42–58, Jan. 1992.
Pfister et al., "Permeation Enhancers Compatible with Transdermal Drug Delivery Systems: Part II: System Design Considerations," *Pharmaceutical Technology*, pp. 54–60, Oct. 1990.
Schulz et al., "Functionality Terminal Polymers via Anionic Methods," *Anionic Polymerization*, American Chemical Society, Chapter 27, pp. 427–440, 1981.

(Continued)

*Primary Examiner*—Edward J. Webman
(74) *Attorney, Agent, or Firm*—Finnegan, Henderson, Farabow, Garrett & Dunner, L.L.P.

(57) ABSTRACT

A transdermal drug delivery device involving a macromonomer-containing acrylate or methacrylate copolymer, a softener, and a drug. Also a pressure sensitive skin adhesive involving a macromonomer containing acrylate or methacrylate copolymer and a softener.

34 Claims, No Drawings

U.S. PATENT DOCUMENTS

| | | | | |
|---|---|---|---|---|
| 5,145,682 A | | 9/1992 | Chien et al. ................ | 424/448 |
| 5,151,271 A | | 9/1992 | Otsuka et al. .............. | 424/443 |
| 5,175,052 A | | 12/1992 | Tokuda et al. .............. | 428/355 |
| 5,176,916 A | | 1/1993 | Yamanaka et al. .......... | 424/448 |
| 5,200,190 A | | 4/1993 | Azuma et al. .............. | 424/443 |
| 5,225,473 A | * | 7/1993 | Duan ......................... | 524/388 |
| 5,229,195 A | | 7/1993 | Maruoka et al. ............ | 428/220 |
| 5,244,677 A | * | 9/1993 | Kreckel ....................... | 424/448 |
| 5,252,395 A | | 10/1993 | Maruoka et al. ............ | 428/355 |
| 5,262,165 A | | 11/1993 | Govil et al. ................ | 424/448 |
| 5,296,230 A | | 3/1994 | Chien et al. ................ | 424/448 |
| 5,298,258 A | | 3/1994 | Akemi et al. ............... | 424/484 |
| 5,302,629 A | * | 4/1994 | Berejka ...................... | 523/111 |
| 5,306,503 A | | 4/1994 | Müller et al. ............... | 424/449 |
| 5,352,516 A | | 10/1994 | Therriault et al. .......... | 428/355 |
| 5,368,860 A | | 11/1994 | Sunami et al. .............. | 424/448 |
| 5,372,819 A | | 12/1994 | Godbey et al. ............. | 424/449 |
| 5,389,376 A | * | 2/1995 | Duan ......................... | 424/448 |
| 5,395,907 A | | 3/1995 | Zajaczkowski ............. | 526/320 |
| 5,508,367 A | | 4/1996 | Zajackowski ............... | 526/320 |
| 5,573,778 A | | 11/1996 | Therriault et al. .......... | 424/448 |
| 5,614,210 A | | 3/1997 | Braun ........................ | 424/448 |
| 5,660,178 A | | 8/1997 | Kantner et al. ............. | 128/640 |

OTHER PUBLICATIONS

"Compliance Test Method," pp. 15–16 from Appln. No. 08/968,519 (TX 1008).
Letters between Herbert H. Mintz and James W. Helliwege, Jan.–Feb. 1999 (TX 1009–1014).
Declaration of Jane Workinger in Support of Therriault Preliminary Motions 2, 3, and 5, Mar. 8, 1999 (TX 1015).
Declaration of Michael J. Zajaczkowski to Correct Inventorship, Mar. 4, 1999 (TX 1016).
Assent of Adhesive Research, Inc. to Correct Inventorship, Mar. 11, 1999 (TX 1017).
Declaration of Donald J. Therriault to Correct Inventorship, Mar. 2, 1999 (TX 1018).
Declaration of Kenneth W. Rodgers to Correct Inventorship, Mar. 9, 1999 (TX 1019).
Petition to Correct Inventorship Pursuant to 37 CFR 1.324, Mar. 9, 1999 (TX 1020).
Substitute Declaration for Patent Application Mar. 1999 (TX 1021).
*Adhesive Bonding*, L. Lee, ed., Secs. 2.2, 3.1–3.3, and 4.1, pp. 36–38, 1991 (TX 1022).
Declaration of Michael J. Zajaczkowski in Support of Therriault Preliminary Motion 4, Mar. 9, 1999 (TX 1023).
Pages 214–217 from Mark T. Keller Notebook, Mar. 28, 1991 (TX 1024).
Declaration of James W. Hellwege in Support of Therriault Miscellaneous Motion 8, Apr. 14, 1999 (TX 1026).
Second Declaration of Michae J. Zajaczkowski in Support of Therriault Second Preliminary Motion 4, Apr. 23, 1999 (TX 1027).
Office Action in Therriault Appln. No. 08/405,872, Sep. 21, 1995 (GX 2001).
Request for Reconsideration in Therriault Appln. No. 08/405,872, Mar. 21, 1996 (GX 2002).
File History of EP Application No. 96301769.4 (EP 732 100), filed Mar. 15, 1996.
Notice Declaring Interference No. 104,263, Nov. 9, 1998.
Therriault Preliminary Motion 1, Mar. 9, 1999.
Therriault Preliminary Motion 2, Mar. 9, 1999.
Therriault Preliminary Motion 3, Mar. 9, 1999.
Therriault Preliminary Motion 4, Mar. 9, 1999.
Therriault Miscellaneous Motion 5, Mar. 9, 1999.
Therriault Motion to Correct Inventorship 6, Mar. 9, 1999.
Supplement to Therriault Motion to Correct Inventorship 6, Mar. 15, 1999.
Garbe Opposition 5, Mar. 26, 1999.
Garbe Motion 1, Mar. 26, 1999.
Proposed Amendment Related to Garbe Motion 1, Mar. 26, 1999.
Therriault Reply 5, Apr. 2, 1999.
Therriault Preliminary Motion 7, Apr. 14, 1969.
Therriault Miscellaneous Motion 8, Apr. 14, 1999.
Order (Paper No. 35), Apr. 6, 1999.
Therriault Consent to Grant of Garbe Preliminary Motion 1, Apr. 19, 1999.
Notice of Withdrawal of Therriault Preliminary Motions 2 and 3 and Miscellaneous Motion 5, Apr. 19, 1999.
Order (Paper No. 40), Apr. 19, 1999.
Order (Paper No. 44), Apr. 21, 1999.
Therriault Second Preliminary Motion 4, Apr. 23, 1999.
Order (Paper No. 47), Apr. 27, 1999.
Withdrawal by Party Therriault of Second Preliminary Motion 4, Jun. 18, 1999.
Stipulation Regarding Therriault Preliminary Motion 6, Jun. 24, 1999.
Garbe Motion No. 2, Jul. 6, 1999.
Proposed Amendment Related to Garbe Motion No. 2, 1999.
Garbe Opposition to Therriault Motion No. 7, Aug. 9, 1999.
Therriault Opposition 2, Aug. 9, 1999.
Therriault Preliminary Motion 9, Aug. 9, 1999.
Therriault Miscellaneous Motion 10, Aug. 9, 1999.
Decision on Motion (Paper No. 60), Aug. 13, 1999.
Therriault Consent to Garbe Motion 2, Aug. 30, 1999.
Garbe Supplemental Opposition to Therriault Motion No. 7, Sep. 10, 1999.
Therriault Reply to Garbe Opposition and Supplemental Opposition to Therriault Motion 7, Sep. 24, 1999.
Order (Paper No. 72), Oct. 21, 1999.
Garbe's List of Pending Claims 1–34, Oct. 26, 1999.
Memorandum Opinion and Order (Paper No. 73), Oct. 27, 1999.
Garbe's Notice Pursuant to 37 C.F.R § 1.632 of Intent to Argue Abandonement, Suppression or Concealment, Apr. 18, 2000.
Garbe's Statement of Issues Under 37 C.F.R. 1.640(b), Jul. 25, 2000.
[Therriault's]Issues to Be Considered Under 37 C.F.R. 1.640(b), Jul. 25, 2000.
Junior Party Principal Brief on Issue Priority, Sep. 15, 2000.
Senior Party Garbe's Opening Brief, Oct. 25, 2000.
Junior Party Brief in Opposition to Senior Party Principal Brief, Nov. 8, 2000.
Senior Party Garbe's Reply Brief, Nov. 22, 2000.
Final Decision and Judgment Under 37 C.F.R. § 1.658(a), Dec. 21, 2000.
Complaint in Civil Action No. 01–0637, Mar. 23, 2001.
Answer in Civil Action No. 01–0637, May 2, 2001.
Defendant Minnesota Mining and Manufacturing Company's Motion Summary Judgment of Suppression or Concealment and Statement of Points and Authorities in Support of Its Motion for Summary Judgment of Suppression or Concealment, Jul. 9, 2001.

Plaintiff Adhesive Research, Inc.'s Statement of Points and Authorities in Opposition to Dependant Minnesota Mining and Manufacturing Company's Motion for Summary Judgment on the Issue of Suppression and Concealment, Jul. 20, 2001.

Submission Adhesives Research of Original Executed Affidavits of George Cramer and Michael Zajaczkowski Supplemental to Opposition to Minnesota Mining and Manufacturing Motion for Summary Judgment, Jul. 24, 2001.

Defendant Minnesota Mining and Manufacturing Company's Reply in Support of its Motion for Summary Judgment of Suppression or Concealment, Jul. 30, 2001.

Transcript of Motions Hearing Before the Honorable James Robertson, Nov. 5, 2001.

Order Denying Defendant's Motion for Partial Summary Judgment, Nov. 7, 2001.

Defendant Minnesota Mining and Manufacturing Company's Motion for Summary Judgment of Suppression or Concealment and Statement of Points and Authorities in Support of its Motion for Summary Judgment of Suppression or Concealment, Jul. 9, 2001.

Join Statement Regarding Status and Proposed Conduct of Proceeding, Aug. 30, 2002.

Joint Motion Setting Briefing Schedule, Sep. 5, 2002.

Minnesota Mining and Manufacturing Company's Motion to Exclude Adhesives Research, Inc.'s Evidence That Allegedly Refutes Suppression or Concealment and Memorandum of Points and Authorities in Support of Minnesota Mining and Mining and Manufacturing Company's Motion to Exclude Adhesives Research, Inc's Evidence That Allegedly Refutes Suppression or Concealment, Oct. 3, 2002.

Minnesota Mining and Manufacturing Company's Motion in the Alternative to Remand the Case to the Patent Office and Memorandum of Points and Authorities in Support of Minnesota Mining and Manufacturing Company's Motion in the Alternative to Remand the Case to the Patent Office, Oct. 3, 2002.

Plaintiff Adhesive Research, Inc.'s Statement of Points and Authorities in Opposition to Motion of Defendant Minnesota Mining and Manufacturing Co. to Exclude Evidence That Allegedly Refutes Suppression or Concealment, Nov. 4, 2002.

Plaintiff Adhesive Research, Inc.'s Statement of Points and Authorities in Opposition Motion of Defendant Minnesota Mining and Manufacturing Co. in the Alternative to Remand the Case to the Patent Office, Nov. 4, 2002.

Reply Memorandum in Support of Minnesota Mining and Manufacturing Company's Motion to Exclude Adhesives Research, Inc.'s Evidence That Allegedly Refutes Suppression or Concealment, Nov. 15, 2002.

Reply Memorandum in Support of Minnesota Mining and Manufacturing Company's Motion in the Alternative to Remand the Case to the Patent Office, Nov. 15, 2002.

Memorandum Opinion and Order, Sep. 2, 2003.

Dependant Minnesota Mining and Manufacturing Company's Motion for Summary Judgment in View of the Court's Sep. 2, 2003 Memorandum Opinion and Order and Memorandum of Points and Authorities in Support of Defendant Minnesota Mining and Manufacturing Company's Motion for Summary Judgment in View of Court's Sep. 2, 2003 Memorandum Opinion and Order, Nov. 21, 2003.

Request for Entry of Judgment in View of No Opposition by Plaintiff to Defendant's Pending Summary Judgment Motion, Dec. 9, 2003.

Order Granting Summary Judgment, Dec. 10, 2003.

* cited by examiner

MATRIX FOR TRANSDERMAL DRUG DELIVERY

This application is a continuation, of application Ser. No. 08/523,762 filed 9/5/95 now abandoned, which was a continuation-in-part of application Ser. No. 08/305,833 filed 9/14/94, abandoned.

BACKGROUND OF THE INVENTION

1. Field of the Invention

This invention relates to drug containing matrices for use in transdermal drug delivery devices. In another aspect this invention relates to pressure sensitive skin adhesives. In yet another aspect this invention relates to pharmaceutical formulations involving a pressure sensitive skin adhesive layer.

2. Description of the Related Art

Transdermal drug delivery devices are designed to deliver a therapeutically effective amount of drug across the skin of a patient. Devices known to the art include reservoir type devices involving membranes that control the rate of drug release to the skin and devices involving a dispersion of the drug in a matrix. Certain acrylic copolymers have been used as matrices for delivery of specific drugs. It is critical in such devices that intimate skin contact be achieved and maintained between the skin and the drug-containing matrix. Thus the range of copolymers that are suitable for use as matrices is limited by the ability of the copolymer to comply to the surface of the skin and still release cleanly from the skin. Moreover, the skin presents a substantial barrier to ingress of foreign substances such as drugs into the body. It is therefore often desirable or necessary to incorporate certain materials that enhance the rate at which the drug passes through the skin.

Certain transdermal drug delivery devices have incorporated pressure sensitive adhesive ("PSA") matrices. Fundamentally, PSA's require a balance of viscous and elastic properties which result in a four-fold balance of adhesion, cohesion, stretchiness, and elasticity. In essence, PSA products have sufficient cohesiveness and elasticity so that, despite their tackiness, they can be handled with the fingers and removed from the skin without leaving substantial residue.

SUMMARY OF THE INVENTION

This invention provides a transdermal drug delivery device, comprising:
(1) a backing;
(2) a matrix adhered to one side of the backing and comprising
 (a) a copolymer comprising
  (i) one or more A monomers selected from the group consisting of alkyl acrylates containing 4 to 10 carbon atoms in the alkyl group and alkyl methacrylates containing 4 to 10 carbon atoms in the alkyl group; and
  (ii) optionally one or more ethylenically unsaturated B monomers copolymerizable with the A monomer; and
  (iii) a macromonomer, preferably a substantially linear macromonomer, copolymerizable with the A and B monomers defined above and having a molecular weight in the range 500–500,000;
 (b) a softener dissolved in the copolymer; and,
 (c) if the softener is not therapeutically effective, a therapeutically effective amount of a drug, wherein the structure and amount of the comonomers in the copolymer, the inherent viscosity of the copolymer, and the amount and structure of the drug and the softener are such as to provide the matrix with a compliance value in the range $2 \times 10^{-6}$ cm$^2$/dyne to about $4 \times 10^{-3}$ cm$^2$/dyne.

It has been found that the copolymer and the softener as defined above can be selected such that the resulting composition adheres to the skin. Accordingly this invention also provides a pressure sensitive skin adhesive comprising:
(1) a copolymer comprising
 (a) one or more A monomers selected from the group consisting of alkyl acrylates containing 4 to 10 carbon atoms in the alkyl group and alkyl methacrylates containing 4 to 10 carbon atoms in the alkyl group; and
 (b) optionally one or more ethylenically unsaturated B monomers copolymerizable with the A monomer; and
 (c) a substantially linear macromonomer copolymerizable with the A and B monomers defined above and having a molecular weight in the range 500–500,000; and
(2) a softener dissolved in the copolymer,
 wherein the structure and amount of the comonomers in the copolymer, the inherent viscosity of the copolymer, and the amount and structure of the softener are such as to provide the pressure sensitive skin adhesive with a compliance value in the range $2 \times 10^{-6}$ cm$^2$/dyne to about $4 \times 10^{-3}$ cm$^2$/dyne.

The invention provides a transdermal drug delivery device that allows dissolution of drug and relatively heavy loading with oily excipients, maintains contact with the skin, and can be removed cleanly from the skin. The pressure sensitive skin adhesives of the invention provide these advantages and in addition adhere to the skin.

DETAILED DESCRIPTION OF THE INVENTION

The term "lower alkyl" as used herein means straight chain or branched chain alkyl containing 1 to 4 carbon atoms.

The present invention provides a transdermal drug delivery device having a backing and a matrix adhered to one side thereof It can be adhered directly to a backing or it can be adhered indirectly to a backing via an intermediate layer.

The matrix contains a copolymer as defined above and a softener. The matrix is preferably a pressure sensitive skin adhesive. In addition, the matrix (whether adhesive or not) can be removed cleanly from the skin.

The copolymer utilized in the practice of the invention should be substantially chemically inert to other components utilized in conjugation therewith (e.g., the drugs and/or softeners discussed in detail below). Also the inherent viscosity of the copolymer is such as to ultimately provide a suitable transdermal matrix, preferably a pressure sensitive skin adhesive. Preferably the copolymer has an inherent viscosity in the range 0.2 dl/g to about 2 dl/g, more preferably in the range 0.4 dl/g to 1.4 dl/g.

Suitable copolymers comprise one or more A monomers preferably in an amount about 40 to 95 percent by weight, more preferably about 50 to about 70 percent by weight, based on the total weight of all monomers in the copolymer. The A monomer is selected from the group consisting of alkyl acrylates containing 4 to 10 carbon atoms in the alkyl group and alkyl methacrylates containing 4 to 10 carbon atoms in the alkyl group. Examples of suitable alkyl acrylates and methacrylates are n-butyl, n-pentyl, n-hexyl, isoheptyl, n-nonyl, n-decyl, isohexyl, 2-ethyloctyl, isooctyl and 2-ethylhexyl acrylates and methacrylates. Preferred alkyl acrylates include isooctyl acrylate, 2-ethylhexyl acrylate, butyl acrylate, and cyclohexyl acrylate. The most preferred alkyl acrylate is isooctyl acrylate. Preferred alkyl methacrylates include butyl methacrylate, cyclohexyl methacrylate, isobornyl methacrylate, and methyl methacrylate.

The copolymer further optionally comprises one or more ethylenically unsaturated B monomers copolymerizable with the A monomer. Suitable B monomers include those comprising a functional group selected from the group consisting of carboxylic acid, carboxylic acid ester, hydroxy, sulfonamide, urea, carbamate, carboxamide, amine, oxy, oxo, and cyano. The B monomers are preferably used in a total amount from 0 to about 60 percent by weight, more preferably greater than 25 to about 50 percent by weight, and most preferably greater than 30 to about 50 percent by weight (based on the total weight of all the monomers in the copolymer). Preferred B monomers include but are not limited to acrylic acid, methacrylic acid, maleic acid, a hydroxyalkyl acrylate containing 2 to 4 carbon atoms in the hydroxyalkyl group, a hydroxyalkyl methacrylate containing 2 to 4 carbon atoms in the hydroxyalkyl group, acrylamide, methacrylamide, an alkyl substituted acrylamide containing 1 to 8 carbon atoms in the alkyl group, diacetone acrylamide, a dialkyl acrylamide having 1 or 2 carbon atoms in the alkyl group, N-vinyl-N-methyl acetamide, N-vinyl valerolactam, N-vinyl caprolactam, N-vinyl-2-pyrrolidone, glycidyl methacrylate, alkoxyethyl acrylate containing 1 to 4 carbon atoms in the alkoxy group, alkoxyethyl methacrylate containing 1 to 4 carbon atoms in the alkoxy group, 2-ethoxyethoxyethyl acrylate, furfryl methacrylate, furfryl acrylate, tetrahydrofurfuryl acrylate, tetrahydrofurfryl methacrylate, propylene glycol monomethacrylate, propylene glycol monoacrylate, polyethylene glycol acrylate, polyethylene glycol methyl ether acrylate, polyethylene glycol methacrylate, polyethylene oxide methyl ether acrylate, di(lower)alkylamino ethyl acrylate, di(lower)alkylamino ethyl methacrylate, di(lower) alkylaminopropyl methacrylamide, acrylonitrile, methacrylonitrile, and vinyl acetate.

Particularly preferred B monomers include hydroxyethyl acrylate, acrylamide, hydroxyethyl methacrylate, glyceryl acrylate, N,N-dimethyl acrylamide, 2-ethoxyethoxyethyl acrylate, 2-ethoxyethyl acrylate, tetrahydrofurfuryl acrylate, vinyl acetate and acrylic acid. Most preferred B monomers include hydroxyethyl acrylate and N,N-dimethyl acrylamide, and a combination thereof.

As noted in detail below, the compositions of the invention can contain a relatively high loading of softener. In order to accommodate such loadings the copolymer incorporates a macromonomer, preferably a substantially linear macromonomer, copolymerizable with the A and B monomers defined above and having a molecular weight in the range 500–500,000, preferably 2,000–100,000, and more preferably 5,000–30,000, in an amount (e.g., at least about 0.1 percent by weight based on the total weight of comonomers in the copolymer) effective to control the rheological properties of the copolymer. The macromonomer is generally present in an amount of not more than about 30% by weight based on the total weight of all monomers in the copolymer, more preferably not more than 15%, and most preferably not more than 5%.

The macromonomer can be a compound of the formula

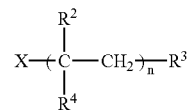

wherein X is a moiety comprising an ethylenically unsaturated group (such as

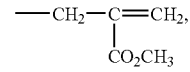

—CH=C(CH$_3$)(CO$_2$CH$_3$), vinyl, or 2-propenyl) copolymerizable with the A and B monomers, $R^2$ is a hydrogen atom or a lower alkyl group, $R^3$ is a lower alkyl group or the residue of a free-radical initiator, n is an integer from 20 to 500 and each $R^4$ is a monovalent radical independently selected from the group consisting of

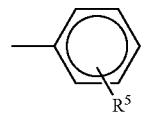

—CN, and —CO$_2$R$^6$ wherein $R^5$ is a hydrogen atom or a lower alkyl group, and $R^6$ is a lower alkyl group. Suitable macromonomers include polymethylmethacrylate, styrene/acrylonitrile, and polystyrene macromonomers. Polymethylmethacrylate macromonomers are preferred.

Exemplary macromonomers include those having a general formula selected from the group consisting of

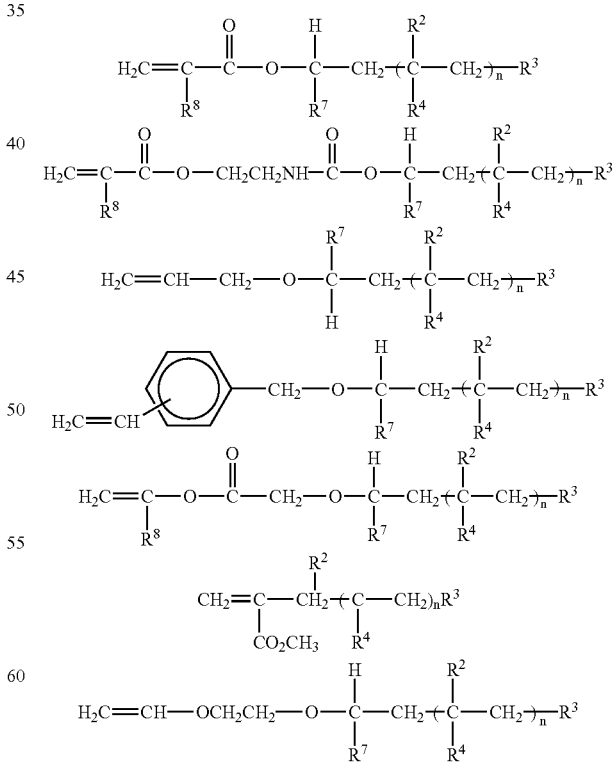

wherein $R^7$ is a hydrogen atom or a lower alkyl group, $R^8$ is hydrogen or methyl, and $R^2$, $R^3$, and $R^4$ are as defined above.

The macromonomers shown in the formulae directly above are functionally terminated polymers having a single functional group and are sometimes identified as a "semitelechelic" polymers. (Vol. 27 "Functionally Terminal Polymers via Anionic Methods" D. N. Schultz et al., pages 427–440, *Anionic Polymerization*, American Chemical Society (1981)). Such macromonomers are known and may be prepared by the method disclosed in U.S. Pat. Nos. 3,786,116, 3,842,059 (both to Milkovich et al.), and 4,732,808 (Krampe et al.), the disclosures of which are incorporated herein by reference for the description of the preparation of the macromonomers. Certain macromonomers are commercially available, for example those polymethylmethacrylate macromonomers sold under the trade designation "ELVACITE" by ICI Acrylics (e.g., ELVACITE 1010, a polymethylmethacrylate macromonomer having an inherent viscosity of 0.070–0.080, a $T_g$ of 105° C., a GPC weight average molecular weight of 7,000–10,000, a GPC number average molecular weight of 2,500–4,000, and a polydispersity of 2.5–3.0, and ELVACITE 1020, a polymethylmethacrylate macromonomer having an inherent viscosity of 0.085–0.10, a $T_g$ of 105° C., a GPC weight average molecular weight of 12,000–15,000, a GPC number average molecular weight of 4,600–6,000, and a polydispersity of 2.5–3.0).

A matrix of the invention further comprises a softener. The softener is dissolved in the matrix. As used herein the term "softener" refers to a generally oily material that raises the compliance value or lowers the glass transition temperature ($T_g$) of the matrix as compared to the copolymer.

Suitable softeners include certain materials that have been used as skin penetration enhancers or solubilizers in transdermal drug delivery systems: Exemplary materials include $C_8$–$C_{22}$ fatty acids such as isostearic acid, octanoic acid, and oleic acid, $C_8$–$C_{22}$ fatty alcohols such as oleyl alcohol and lauryl alcohol, lower alkyl esters of $C_8$–$C_{22}$ fatty acids such as ethyl oleate, isopropyl myristate, butyl stearate, and methyl laurate, di(lower) alkyl esters of $C_6$–$C_8$ diacids such as diisopropyl adipate, monoglycerides of $C_8$–$C_{22}$ fatty acids such as glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, N,N-dimethyldodecylamine-N-oxide, and combinations of the foregoing. Alkylaryl ethers of polyethylene oxide, polyethylene oxide monomethyl ethers, and polyethylene oxide dimethyl ethers are also suitable, as are solubilizers such as dimethyl sulfoxide, glycerol, ethanol, ethyl acetate, acetoacetic ester, N-methyl pyrrolidone, and isopropyl alcohol. Likewise certain drug substances function as softeners, including nicotine, nitroglycerine, chlorpheniramine, nicotinic acid benzyl ester, orphenadrine, scopolamine, and valproic acid.

Preferred softeners include glyceryl monolaurate, diethylene glycol monomethyl ether, tetrahydrofurfuryl alcohol polyethylene glycol ether, diisopropyl adipate, propylene glycol, isopropyl myristate, ethyl oleate, methyl laurate, 2-(2-ethoxyethoxy)ethanol, and oleyl alcohol.

Preferably the softener is present in not more than that amount which causes the matrix to leave substantial copolymer residue on the skin when peeled from the skin.

While many of the softeners enumerated above are known to affect skin penetration rate, certain softeners affect aspects of performance other than and in addition to skin penetration rate. For example, they are useful in softening and/or increasing the compliance value and/or lowering the glass transition temperature of otherwise non-compliant (and therefore non-pressure sensitive adhesive) copolymers, rendering them suitable for use as pressure sensitive skin adhesives. However, the softeners enumerated above are generally oily substances that function as plasticizers when incorporated in a copolymer. Such materials can affect adversely the performance of a transdermal matrix, for example by softening it to the point of cohesive failure (where substantial copolymer residue is left on the skin upon removal of the device from the skin), or by separating from the continuous phase and forming an oily layer that reduces adhesion of an otherwise adhesive matrix. Also, certain softeners (e.g., glyceryl monolaurate, N,N-dimethyldodecylamine-N-oxide) can crystallize in the copolymer, resulting in unstable properties (e.g., unstable drug delivery rates in a transdermal drug delivery device).

Possible adverse effects of softeners notwithstanding, with proper selection of softeners, monomers and relative amounts thereof, and inherent viscosity of the copolymer, softeners can be included in amounts of up to about 60% by weight based on the total weight of the matrix without cohesive failure or crystal formation, and often without loss of suitable skin adhesion. Softener amounts in excess of 20% and preferably less than about 45% by weight based on the total weight of the matrix have been found to be preferred in order to obtain optimal flux rates in transdermal devices containing the hormone levonorgestrel, and amounts in excess of 30% and less than 45% are more preferred.

The properties desirable in a transdermal matrix are well known to those skilled in the art. For example, it is necessary that the matrix remain in intimate contact with the skin in order to deliver drug at a stable rate. It is desirable for a matrix to have sufficiently little cold flow such that it is stable to flow upon storage. It is also preferred that it release cleanly from the skin, and that it adhere to the skin. In order to achieve skin contact, clean release, preferred levels of adhesion, and resistance to cold flow the amount and structure of the comonomers in the copolymer, the inherent viscosity of the copolymer, and the amount and structure of the softener are selected such that the matrix has a compliance value(measured according to the test method set forth in detail below) in the range $2\times10^{-6}$ cm$^2$/dyne to about $4\times10^{-3}$ cm$^2$/dyne, preferably in the range $3\times10^{-6}$ cm$^2$/dyne to about $1\times10^{-3}$ cm$^2$/dyne and even more preferably in the range $1\times10^{-5}$ cm$^2$/dyne to $5\times10^{31\ 4}$ cm$^2$/dyne. Compliance values outside the broad range recited above sometimes are obtained from materials that are suitable matrices, and even for some that are suitable for use as pressure sensitive skin adhesives. However, those matrices having substantially lower compliance values will generally be relatively stiff and have less than optimal skin contact and adhesion to skin. Those having substantially higher compliance values will generally have less than optimal cold flow and might leave substantial residue when removed from the skin. Also, a matrix of the invention that is intended for use as a pressure sensitive skin adhesive preferably has a glass transition temperature of −10° C. or lower.

Particularly suitable compositions can be readily selected for a given set of desired properties considering the effects of comonomers, inherent viscosity, and softeners on the properties of the resulting matrix. Certain of such effects are well known to those skilled in the art, and others are described below:

Strongly hydrogen bonding B monomers have been found to increase the amount of polar or hydrogen bonding substances that can be dissolved in a matrix and to decrease the amount of generally nonpolar substances that can be dissolved. Further, a strongly hydrogen bonding copolymer will be a relatively less compliant material. Therefore if B monomers such as acrylic acid or acrylamide are used a lesser amount of macromonomer will be required in order to lower compliance sufficiently to avoid cohesive failure.

Macromonomers also decrease compliance. Therefore a given target compliance value can often be achieved using a lower inherent viscosity A/B copolymer combination and a greater amount of macromonomer, or a higher inherent viscosity A/B combination and less macromonomer.

A relatively high compliance pressure sensitive skin adhesive involving a macromonomer will generally have better adhesive properties than an A/B copolymer having the same compliance value. Increasing macromonomer content generally increases the amount of softener that can be loaded into a pressure sensitive skin adhesive without cohesive failure. Increasing inherent viscosity will also tend to allow higher softener loading without cohesive failure.

A change that would increase inherent viscosity of a copolymer (such as increased molecular weight through selection of polymerization conditions and/or solvent ratios) will generally decrease compliance.

Further conventional components, such as stabilizers and reinforcers (e.g., colloidal silicon dioxide), can be incorporated into the matrix if necessary or desirable.

Of course such high levels of certain individual softeners (e.g., N,N-dimethyldodecylamine-N-oxide) are to be avoided in order to avoid excessive skin irritation.

The matrix of a transdermal drug delivery device of the invention further comprises a drug. Suitable drugs include those active substances enumerated above in connection with softeners, as well as antiinflammatory drugs, both steroidal (e.g., hydrocortisone, prednisolone, triamcinolone) and nonsteroidal (e.g., naproxen, piroxicam); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone, testosterone, estradiol, levonorgestrel); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinoline-4-amine, and other compounds disclosed in U.S. Pat. No. 4,689,338, incorporated herein by reference, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones, LHRH); cardioactive products such as atriopeptides; proteinaceous products (e.g., insulin); enzymes (e.g., anti-plaque enzymes, lysozyme, dextranase); antinauseants (e.g., scopolomine); anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatriptan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; and the like, as well as pharmaceutically acceptable salts and esters thereof.

The drug is present in a transdermal delivery device of the invention in a therapeutically effective amount, i.e., an amount effective to bring about a desired therapeutic result in the treatment of a condition. The amount that constitutes a therapeutically effective amount varies according to the particular drug incorporated in the device, the condition being treated, any drugs being coadministered with the selected drug, desired duration of treatment, the surface area of the skin over which the device is to be placed, and other components of the transdermal delivery device. Accordingly it is not practical to enumerate particular preferred amounts but such can be readily determined by those skilled in the art with due consideration of these factors. Generally, however, a drug is present in a transdermal device of the invention in an amount of about 0.01 to about 30 percent by weight based on the total weight of the matrix. In a preferred embodiment the drug is substantially fully dissolved, and the matrix is substantially free of solid undissolved drug.

A transdermal delivery device or an adhesive coated sheet material of the invention also comprises a backing. The backing is flexible such that the device conforms to the skin. Suitable backing materials include conventional flexible backing materials used for pressure sensitive tapes, such as polyethylene, particularly low density polyethylene, linear low density polyethylene, high density polyethylene, polyester, polyethylene terephthalate, randomly oriented nylon fibers, polypropylene, ethylene-vinyl acetate copolymer, polyurethane, rayon and the like. Backings that are layered, such as polyethylene-aluminum-polyethylene composites, are also suitable. The backing should be substantially inert to the ingredients of the matrix layer.

The copolymers described above for use in a device of the invention can be prepared by methods well known to those skilled in the art and described, for example, in U.S. Patent RE 24,906 (Ulrich) and U.S. Pat. No. 4,732,808 (Krampe at al.), the disclosures of which are incorporated herein by reference.

Matrices of the invention can be used in the form of an adhesive coated sheet material. Such sheet materials are preferably prepared by combining the copolymer, the softener, and any additional components (e.g., a drug) with an organic solvent (e.g., ethyl acetate, methanol, acetone, 2-butanone, ethanol, isopropyl alcohol, toluene, alkanes, or a mixture thereof) to afford a coating formulation. The total solids content of the coating formulation is preferably in a range of about 15 to 40 percent by weight, and more preferably in the range of about 20 to 35 percent by weight, based on the total weight of the coating formulation. The components of the coating formulation are combined and mixed (e.g., by shaking or rolling) until a homogeneous formulation is obtained, then allowed to stand to dissipate air bubbles. The resulting coating formulation is knife coated onto a suitable release liner to provide a predetermined uniform thickness of the coating formulation. Suitable release liners include conventional release liners comprising a known sheet material such as a polyester web, a polyethylene web, or a polystyrene web, or a polyethylene-coated paper, coated with a suitable fluoropolymer or silicone based coating. The coated release liner is dried and then laminated onto a backing material using conventional methods. Alternatively the coating formulation can be coated directly onto a backing. A transdermal device involving a matrix that is not a skin adhesive can be fixed to the skin by conventional means such as a peripheral ring of a pressure sensitive skin adhesive.

Adhesive coated sheet materials of the invention can be made in the form of an article such as a tape, a patch, a sheet, a dressing or any other form known to those skilled in the art. Transdermal drug delivery devices generally are made in the form of a patch of a size suitable to deliver a preselected amount of a drug through the skin. Generally the transdermal device will have a surface area of about 1 cm² to about 40 cm².

The examples set forth below are intended to illustrate the invention.

Compliance Test Method

The compliance values given in the examples below were obtained using a modified version of the Creep Compliance Procedure described in U.S. Pat. No. 4,737,559 (Kellen), the disclosure of which is incorporated herein by reference. The release liner is removed from a sample of the material to be tested. The exposed adhesive surface is folded back on itself in the lengthwise direction to produce a "sandwich" configuration, i.e., backing/adhesive/backing. The "sandwiched" sample is passed through a laminator, or alternatively rolled with a hand-operated roller, then two test samples of equal area are cut using a rectangular die. One test sample is centered on a first stationary plate of a shear-creep rheometer with the long axis of the test sample centered on the short axis of the plate. The small, non-stationary plate of the shear-creep rheometer is centered over the first sample on the first stationary plate such that the hook is facing up and toward the front of the rheometer. The second test sample is centered on the upper surface of the small, non-stationary plate matching the axial orientation of the first test sample. A second stationary plate is placed over the second test sample and the entire assembly is clamped into place. The end of the small, non-stationary plate that is opposite the end with the hook is connected to a chart recorder. A string is connected to the hook of the small, non-stationary plate and extended over the front pulley of the rheometer. A weight (e.g., 500 g) is attached to the free end of the string. The chart recorder is started and at the same time the weight is quickly released so that it hangs free. The weight is removed after exactly 3 minutes has elapsed. The displacement is read from the chart recorder. The compliance is then calculated using the equation:

$$J = 2\frac{AX}{hf}$$

where A is the area of one face of the test sample, h is the thickness of the adhesive mass (i.e., two times the matrix thickness of the sample being tested), X is the displacement and f is the force due to the mass attached to the string. Where A is expressed in cm², h in cm, X in cm and f in dynes, the compliance value is given in cm²/dyne.

Determination of Isopropyl Myristate Content

The amount of isopropyl myristate present in a pressure sensitive skin adhesive composition was determined using the following test method. The release liner is removed from a sample of the material to be tested. The adhesive coating is manually scraped from the backing film. A 15 mg portion of the adhesive coating is placed into a clean sample vial. Tetrahydrofuran (2 mL containing 0.10 mg/mL of lauryl acrylate which serves as an internal standard) is added and the sample is mixed until all of the adhesive coating is dissolved. A portion of the solution is placed in an autosampler vial and analyzed by gas chromatography using the following conditions: Instrument: HP5890;Column: DB-5, 30 meter, 0.25 μM film, 0.25 mm I.D.; Temperature Program: Initial 100° C., ramp 10° C./min to 300° C., hold 2 min; Injection: 2 μL, split 25/1, 300° C.; Detection: FID, 300° C. Isopropyl myristate standards are prepared using copolymer samples containing no isopropyl myristate. Separate standard curves are prepared for each copolymer. Each sample is run in duplicate.

Determination of Oleyl Alcohol Content

The amount of oleyl alcohol present in a pressure sensitive skin adhesive composition was determined using the following test method. The release liner is removed from a sample of the material to be tested. The adhesive coating is manually scraped from the backing film. A 15 mg portion of the adhesive coating is placed into a clean sample vial. Tetrahydrofuran (10 mL containing 0.1 mg/mL of dodecyl alcohol which serves as an internal standard) is added and the sample is mixed until all of the adhesive coating is dissolved. A portion of the solution is placed in an autosampler vial and analyzed by gas chromatography using the following conditions: Instrument: HP5890;Column: DB-wax, 15 meter, 0.25 μM film, 0.25 mm I.D.; Temperature Program: Initial 60° C., ramp 7° C./min to 250° C., hold 2 min; Injection: 2 μL, split 25/1, 250° C.; Detection: FID, 250° C. Oleyl alcohol standards are prepared using copolymer samples containing no oleyl alcohol. Separate standard curves are prepared for each copolymer. Each sample is run in duplicate.

Preparation of Copolymers

The copolymers used in the examples that follow were prepared generally according to the methods described below. The inherent viscosity values which are reported were measured by conventional means using a Cannon-Fenske #50 viscometer in a water bath controlled at 27° C. to measure the flow time of 10 milliliters of a polymer solution (0.15–0.25 g per deciliter of polymer in ethyl acetate, unless other wise indicated). The test procedure followed and the apparatus used are described in detail in "Textbook of Polymer Science", F. W. Billmeyer, Wiley Interscience, Second Edition, 1971, Pages 84 and 85.

Preparation of Isooctyl Acrylate: Dimethylacrylamide: Hydroxyethyl Acrylate: Polymethylmethacrylate Macromonomer (60/15/15/10) Copolymer Isooctyl acrylate (141.0 g), N,N-dimethylacrylamide (35.25 g), hydroxyethyl acrylate (35.25 g), ELVACITE™ 1010 polymethylmethacrylate macromonomer (23.50 g, ICI), ethyl acetate (251.75 g), isopropanol (13.25 g) and 2,2'-azobis (2,4-dimethylpentanenitrile) (0.47 g, VAZO™ 52 available from DuPont) were charged into a one liter bottle. The mixture was deoxygenated by purging with nitrogen (1L/min) for 2 minutes. The bottle was sealed and placed in a rotating water bath at 45° C. for 24 hours. The bottle was removed, opened, charged with an additional 0.47 g of VAZO 52, repurged with nitrogen as before, sealed and placed in the launderometer for an additional 24 hours. The percent solids of the resulting solution of copolymer was 45.51%. The inherent viscosity was 0.469 deciliter/gram in ethyl acetate at 0.25 g/dl.

Preparation of Isooctyl Acrylate: Dimethylacrylamide: Polymethylmethacrylate Macromonomer (50/40/10) Copolymer Isooctyl acrylate (117.5 g), N,N-dimethylacrylamide (94.0 g), ELVACITE™ 1010 polymethylmethacrylate macromonomer (23.5 g), ethyl acetate (251.75 g), isopropanol (13.25 g) and VAZO 52 (0.47 g) were charged into a one liter bottle. The mixture was deoxygenated by purging with nitrogen (1L/min) for 2 minutes. The bottle was sealed and placed in a rotating water bath at 45° C. for 24 hours. The bottle was removed, opened, charged with an additional 0.47 g of VAZO 52, repurged with nitrogen as before, sealed and placed in the launderometer for an additional 24 hours. The percent solids of the resulting solution of copolymer was 46.19%. The inherent viscosity was 0.532 dl/g in ethyl acetate at 0.25 g/dl.

Preparation of Isooctyl Acrylate: Dimethylacrylamide: Polymethylmethacrylate Macromonomer (63/27/10) Copolymer Isooctyl acrylate (157.5 g), N,N-dimethylacrylamide (67.5 g), ELVACITE 1010 macromonomer (25.0 g), ethyl acetate (261.25 g), isopropanol (13.75 g) and VAZO 52 (0.5 g) were charged into a one liter bottle. The mixture was deoxygenated by purging with nitrogen (1L/min) for 3 minutes. The bottle was sealed and placed in a rotating water bath at 45° C. for 24 hours. The bottle was removed, opened, charged with an additional 0.5 g of VAZO 52, repurged with nitrogen as before, sealed and placed in the launderometer for an additional 24 hours. The percent solids of the resulting solution of copolymer was 47.8%. The inherent viscosity was 0.394 dl/g in ethyl acetate at 0.15 g/dl.

Preparation of Isooctyl Acrylate: Hydroxyethyl Acrylate: Polymethylmethacrylate Macromonomer (55/40/5) Copolymer Molecular sieves (50 g of 8–12 mesh, 4A, 1.6 mm beads) were added to each of 4 quart (0.95 L) wide mouth jars. The jars were filled with isooctyl acrylate, hydroxyethyl acrylate, ethyl acetate, and isopropanol respectively. The jars were tightly capped and allowed to stand for at least 24 hours. The molecular sieves were then removed by filtration through Whatman filter paper No. 4. The "dry" monomers and solvents were then stored in tightly capped bottles until used to prepare copolymer. Isooctyl acrylate (137.5 g), hydroxyethyl acrylate (100.0 g), ELVACITE™ 1010 polymethylmethacrylate macromonomer (12.5 g), ethyl acetate (318.75 g), isopropanol (56.25 g) and VAZO 52 (0.5 g) were charged into a one liter bottle. The mixture was deoxygenated by purging with nitrogen (1L/min) for 3 minutes. The bottle was sealed and placed in a rotating water bath at 45° C. for 24 hours. The bottle was removed, opened, charged with an additional 0.5 g of VAZO 52, repurged with nitrogen as before, sealed and placed in the launderometer for an additional 24 hours. The percent solids of the resulting solution of copolymer was 39.30%. The inherent viscosity was 0.335 dl/g in ethyl acetate at 0.15 g/dl.

Preparation of Isooctyl Acrylate: Hydroxyethyl acrylate: Polystyrene Macromonomer (54/36/10) Copolymer Isooctyl acrylate (135 g), hydroxyethyl acrylate (90 g), polystyrene macromonomer (25.0 g), ethyl acetate (356.25 g), isopropanol (18.75 g) and VAZO 52 (0.5 g) were charged into a one liter bottle. The mixture was deoxygenated by purging with nitrogen (1L/min) for 3 minutes. The bottle was sealed and placed in a rotating water bath at 45° C. for 24 hours. The bottle was removed, opened, charged with an additional 0.5 g of VAZO 52, repurged with nitrogen as before, sealed and placed in the launderometer for an additional 24 hours. The percent solids of the resulting solution of copolymer was 41.2%. The inherent viscosity was 0.75 dl/g in ethyl acetate at 0.15 g/dl.

Preparation of Isooctyl Acrylate: Hydroxyethyl acrylate: Polystyrene Macromonomer (54/36/10) Copolymer Isooctyl acrylate (135 g), hydroxyethyl acrylate (90 g), polystyrene macromonomer (25.0 g), ethyl acetate (318.75 g), isopropanol (56.25 g) and VAZO 52 (0.5 g) were charged into a one liter bottle. The mixture was deoxygenated by purging with nitrogen (1L/min) for 3 minutes. The bottle was sealed and placed in a rotating water bath at 45° C. for 24 hours. The bottle was removed, opened, charged with an additional 0.5 g of VAZO 52, repurged with nitrogen as before, sealed and placed in the launderometer for an additional 24 hours. The percent solids of the resulting solution of copolymer was 39.6%. The inherent viscosity was 0.29 dl/g in ethyl acetate at 0.15 g/dl.

Preparation of Isooctyl Acrylate:Polystyrene Macromonomer (95/5) Copolymer

Isooctyl acrylate (237.5 g), polystyrene macromonomer (12.5 g), ethyl acetate (261.25 g), isopropanol (13.75 g) and VAZO 52 (0.5 g) were charged into a one liter bottle. The mixture was deoxygenated by purging with nitrogen (1L/min) for 3 minutes. The bottle was sealed and placed in a rotating water bath at 45° C. for 24 hours. The bottle was removed, opened, charged with an additional 0.5 g of VAZO 52, repurged with nitrogen as before, sealed and placed in the launderometer for an additional 24 hours. The percent solids of the resulting solution of copolymer was 47.5%. The inherent viscosity was 0.45 dl/g in ethyl acetate at 0.15 g/dl.

Preparation of Isooctyl Acrylate: Vinyl Acetate: Polystyrene Macromonomer (61/37/2) Copolymer Isooctyl acrylate (134.2 g), vinyl acetate (81.4 g), polystyrene macromonomer (4.4 g), 2,2'-azobis(isobutyronitrile) (0.55 g), ethyl acetate (126.0 g), and toluene (54.0 g) were charged into a one liter bottle. The mixture was deoxygenated by purging with nitrogen (1 L/min) for 2 minutes. The bottle was sealed and placed in a rotating water bath at 60° C. for 24 hours. The resulting copolymer solution was diluted with ethyl acetate (150 mL). The inherent viscosity in ethyl acetate at 0.2 g/dl was measured at 0.87 dl/g.

Preparation of Isooctyl Acrylate: Vinyl Acetate: Polystyrene Macromonomer (61/37/2) Copolymer Isooctyl acrylate (134.2 g), vinyl acetate (81.4 g), polystyrene macromonomer (4.4 g), 2,2'-azobis(isobutyronitrile) (0.55 g), ethyl acetate (144.0 g), and toluene (36.0 g) were charged into a one liter bottle. The mixture was deoxygenated by purging with nitrogen (1 L/min) for 2 minutes. The bottle was sealed and placed in a rotating water bath at 60° C. for 24 hours. The resulting copolymer solution was diluted with ethyl acetate (150 mL). The inherent viscosity in ethyl acetate at 0.2 g/dl was measured at 1.02 dl/g.

Preparation of Isooctyl Acrylate: Vinyl Acetate: Polystyrene Macromonomer (58/37/5) Copolymer Isooctyl acrylate (127.6 g), vinyl acetate (81.4 g), polystyrene macromonomer (11.0 g), 2,2'-azobis (isobutyronitrile) (0.55 g), ethyl acetate (126.0), and toluene (54.0 g) were charged into a one liter bottle. The mixture was deoxygenated by purging with nitrogen (1 L/min) for 2 minutes. The bottle was sealed and placed in a rotating water bath at 60° C. for 24 hours. The resulting copolymer solution was diluted with ethyl acetate (150 mL). The inherent viscosity in ethyl acetate at 0.2 g/dl was measured at 0.89 dl/g.

Preparation of Isooctyl Acrylate: Vinyl Acetate: Polystyrene Macromonomer (58/37/5) Copolymer Isooctyl acrylate (127.6 g), vinyl acetate (81.4 g), polystyrene macromonomer (11.0 g), 2,2'-azobis (isobutyronitrile) (0.55 g), ethyl acetate (144.0), and toluene (36.0 g) were charged into a one liter bottle. The mixture was deoxygenated by purging with nitrogen (1 L/min) for 2 minutes. The bottle was sealed and placed in a rotating water bath at 60° C. for 24 hours. The resulting copolymer solution was diluted with ethyl acetate (150 mL). The inherent viscosity in ethyl acetate at 0.2 g/dl was measured at 1.02 dl/g.

Preparation of Isooctyl Acrylate: Vinyl Acetate: Polymethylmethacrylate Macromonomer (58/37/5) Copolymer Isooctyl acrylate (145.0 g), vinyl acetate (92.5 g), ELVACITE™ 1020 polymethylmethacrylate macromonomer (12.5 g), 2,2'-azobis (2,4-dimethylpentanenitrile) (0.5 g), and ethyl acetate (282.0) were charged into a one liter bottle. The mixture was deoxygenated by purging with nitrogen (1 L/min) for 3 minutes. The bottle was sealed and placed in a rotating water bath at 45° C. for 24 hours. The bottle was removed from the bath, opened, charged with an additional 0.5 g of 2,2'-azobis(2,4-dimethylpentanenitrile), deoxygenated as before, sealed and returned to the rotating water bath for an additional 24 hours. The inherent viscosity in ethyl acetate at 0.15 g/dl was measured at 1.05 dl/g.

Preparation of Isooctyl Acrylate: Vinyl Acetate: Polymethylmethacrylate Macromonomer (58/37/5) Copolymer Isooctyl acrylate (145.0 g), vinyl acetate (92.5 g), ELVACITE™ 1020 polymethylmethacrylate macromonomer (12.5 g), 2,2'-azobis (2,4-dimethylpentanenitrile) (0.5 g), and ethyl acetate (250.0) were charged into a one liter bottle. The mixture was deoxygenated by purging with nitrogen (1 L/min) for 3 minutes. The bottle was sealed and placed in a rotating water bath at 45° C. for 24 hours. The bottle was removed from the bath, opened, charged with an additional 0.5 g of 2,2'-azobis(2,4-dimethylpentanenitrile), deoxygenated as before, sealed and returned to the rotating water bath for an additional 24 hours. The inherent viscosity in ethyl acetate at 0.15 g/dl was measured at 1.15 dl/g.

Preparation of Isooctyl Acrylate: Vinyl Acetate: Polymethylmethacrylate Macromonomer (53/37/10) Copolymer Isooctyl acrylate (132.5 g), vinyl acetate (92.5 g), ELVACITE™ 1020 polymethylmethacrylate macromonomer (25.0 g), 2,2'-azobis (2,4-dimethylpentanenitrile) (0.5 g), and ethyl acetate (230.8) were charged into a one liter bottle. The mixture was deoxygenated by purging with nitrogen (1 L/min) for 3 minutes. The bottle was sealed and placed in a rotating water bath at 45° C. for 24 hours. The bottle was removed from the bath, opened, charged with an additional 0.5 g of 2,2'-azobis(2,4-dimethylpentanenitrile), deoxygenated as before, sealed and returned to the rotating water bath for an additional 24 hours. The inherent viscosity in ethyl acetate at 0.15 g/dl was measured at 0.815 dl/g.

Preparation of Isooctyl Acrylate: Vinyl Acetate: Polymethylmethacrylate Macromonomer (53/37/10) Copolymer Isooctyl acrylate (132.5 g), vinyl acetate (92.5 g), ELVACITE™ 1020 polymethylmethacrylate macromononier (25.0 g), 2,2'-azobis (2,4-dimethylpentanenitrile) (0.5 g), and ethyl acetate (204.5) were charged into a one liter bottle. The mixture was deoxygenated by purging with nitrogen (1 L/min) for 3 minutes. The bottle was sealed and placed in a rotating water bath at 45° C. for 24 hours. The bottle was removed from the bath, opened, charged with an additional 0.5 g of 2,2'-azobis (2,4-dimethylpentanenitrile), deoxygenated as before, sealed and returned to the rotating water bath for an additional 24 hours. The inherent viscosity in ethyl acetate at 0.15 g/dl was measured at 0.92 dl/g.

Preparation of "Dried" Adhesive

Dried adhesive is prepared by knife coating a 25 to 50 percent solids solution of the adhesive copolymer at a thickness of 20 to 25 mil (500 to 635 μM) onto a release liner. The adhesive coated release liner is oven dried (e.g. 4 min at 110° F. (43° C.), 2 minutes at 185° F. (85° C.), and 10 minutes at 300° F. (149° C.) to remove solvvent and reduce the amount of residual monmers. The dried adhesive copolymer is stripped off the release liner and stored in a glass container.

In the examples that follow all percentages are weight/weight unless otherwise indicated. The weight percentages of the formulations after drying are calculated values, unless otherwise indicated, and assume that only solvent was evaporated during the drying process. The abbreviations IOA, HEA, DMACM, PSMac, PMMAMac, and VoAc are used for isooctyl acrylate, hydroxyethyl acrylate, dimethylacrylamide, polystyrene macromonomer, polymethylmethacrylate macromonomer, and vinyl acetate respectively. The polystyrene macromonomer used in the copolymers in the examples below is that macromonomer designated as Example M-1 in U.S. Pat. No. 4,732,808 (Krampe). Except as noted, the polymethylmethacrylate macromonomer used was ELVACITE 1010. The abbreviations BS, DDAO, DGME, DIPA, EO, GML, IPM, ISA, LG, ML, OA and PG are used for butyl stearate, N,N-dimethyldodecylamine-N-oxide, diethylene glycol monoethyl ether, diisopropyl adipate, ethyl oleate, glyceryl monolaurate, isopropyl myristate, isostearic acid, lauryl glycol, methyl laurate, oleyl alcohol and propylene glycol respectively. The abbreviation LN is used for levonorgestrel.

EXAMPLE 1

Copolymer (50 g of 54/36/10 IOA/HEA/PSMac, 41% solids in 95/5 ethyl acetate/isopropanol, inherent viscosity ("iv")=0.75 dl/g) and isopropyl myristate (1.08 g) were combined in a glass jar. The jar was capped and placed on a roller for about 24 hours. The resulting formulation was knife coated at a wet thickness of 12 mil (305 μM) onto a silicone release liner [5 mil (127 μM) Daubert PESTER]. The coated release liner was oven dried at 110° F. (43° C.) for 4 minutes then at 180° F. (82° C.) for 4 minutes. The resulting coating contained 95 percent 54/36/10 IOA/HEA/PSMac copolymer and 5 percent isopropyl myristate. The coated liner was laminated to the corona treated side of a 3 mil (76 μM) polyethylene film. The compliance was measured using the test method described above and found to be $0.42 \times 10^{-5}$ cm$^2$/dyne (average of three independent determinations).

EXAMPLES 2–33

Using the general method of Example 1, a series of coated sheet materials in which the copolymer, softener and amount of softener were varied was prepared. The copolymer, identity and amount of softener, wet coating thickness, and the compliance values are shown in Table 1. Unless otherwise indicated, each J-value is the average of three independent determinations. When the compliance was "not run", the formulation was too soft to be tested.

TABLE 1

| Example Number | Copolymer Type | iv (dl/g) | Softener | Wet Coating Thickness (mil/μM) | J-value (× 10⁻⁵ cm²/dyne) |
|---|---|---|---|---|---|
| 2 | 54/36/10 IOA/HEA/PSMac | 0.75 | 10% IPM | 12/305 | 0.57 |
| 3 | 54/36/10 IOA/HEA/PSMac | 0.75 | 13% IPM | 12/305 | 0.57 |
| 4 | 54/36/10 IOA/HEA/PSMac | 0.75 | 17% IPM | 10/254 | 0.80 |
| 5 | 54/36/10 IOA/HEA/PSMac | 0.75 | 20% IPM | 10/254 | 1.12 |
| 6 | 54/36/10 IOA/HEA/PSMac | 0.75 | 25% IPM | 8/203 | 2.26 |
| 7 | 54/36/10 IOA/HEA/PSMac | 0.29 | 5% IPM | 12/305 | 1.09 |
| 8 | 54/36/10 IOA/HEA/PSMac | 0.29 | 10% IPM | 12/305 | 1.65 |
| 9 | 54/36/10 IOA/HEA/PSMac | 0.29 | 13% IPM | 12/305 | 1.83 |
| 10 | 54/36/10 IOA/HEA/PSMac | 0.29 | 17% IPM | 10/254 | 2.13[1] |
| 11 | 54/36/10 IOA/HEA/PSMac | 0.29 | 20% IPM | 10/254 | 3.87[2] |
| 12 | 54/36/10 IOA/HEA/PSMac | 0.29 | 25% IPM | 8/203 | 14.2 |
| 13 | 51/34/15 IOA/HEA/PMMAMac | 0.38 | 10% IPM | 12/305 | 0.28 |
| 14 | 51/34/15 IOA/HEA/PMMAMac | 0.38 | 20% IPM | 10/254 | 0.46 |
| 15 | 51/34/15 IOA/HEA/PMMAMac* | 0.42 | 10% IPM | 12/305 | 0.28 |
| 16 | 51/34/15 IOA/HEA/PMMAMac* | 0.42 | 20% IPM | 10/254 | 0.38 |
| 17 | 72/13/15 IOA/HEA/PMMAMac | 0.36 | 10% IPM | 12/305 | 0.38 |
| 18 | 72/13/15 IOA/HEA/PMMAMac | 0.36 | 20% IPM | 10/254 | 0.53 |
| 19 | 85/15 IOA/PMMAMac | 0.48 | 10% IPM | 12/305 | not run |
| 20 | 85/15 IOA/PMMAMac | 0.48 | 20% IPM | 10/254 | off scale |
| C1 | 57/38/5 IOA/HEA/PSMac | 0.32 | none | 6/152 | 1.29 |
| 21 | 54/36/10 IOA/HEA/PSMac | 0.29 | 30% IPM | 6/152 | 66.8 |
| 22 | 51/34/15 IOA/HEA/PSMac | 0.28 | 30% IPM | 6/152 | 18.2 |
| 23 | 51/34/15 IOA/HEA/PSMac | 0.28 | 15% IPM | 10/254 | 0.76 |
| C2 | 57/38/5 IOA/HEA/PSMac | 0.65 | none | 6/152 | 0.57 |
| 24 | 54/36/10 IOA/HEA/PSMac | 0.75 | 35% IPM | 6/152 | 11.2 |
| 25 | 51/34/15 IOA/HEA/PSMac | 0.73 | 50% IPM | 6/152 | 155 |
| 26 | 51/34/15 IOA/HEA/PSMac | 0.73 | 40% IPM | 6/152 | 27.8 |
| 27 | 51/34/15 IOA/HEA/PSMac | 0.73 | 30% IPM | 6/152 | 2.36 |
| 28 | 51/34/15 IOA/HEA/PSMac | 0.73 | 50% OA | 10/254 | not run |
| 29 | 51/34/15 IOA/HEA/PSMac | 0.73 | 40% OA | 10/254 | 3.59 |
| 30 | 51/34/15 IOA/HEA/PSMac | 0.73 | 30% OA | 10/254 | 0.64 |
| 31 | 51/34/15 IOA/HEA/PSMac | 0.73 | 20% OA | 10/254 | 0.42 |
| 32 | 51/34/15 IOA/HEA/PSMac | 0.73 | 40% ISA | 10/254 | 0.79 |
| 33 | 51/34/15 IOA/HEA/PSMac | 0.73 | 40% BS | 10/254 | not run |

[1]average of 2 determinations
[2]average of 4 determinations
PMMAMac* ELVACITE 1020

EXAMPLES 34–38

Using the general method of Example 1, a series of coated sheet materials in which the copolymer was varied but the amount of IPM was theoretically held constant was prepared. The copolymer and amount (both calculated and determined using a modification of the method described above) of IPM, wet coating thickness, and the compliance values are shown in Table 2. In the modified analysis procedure, sample preparation involved combining 2 mL ethyl acetate containing 0.05 mg/mL lauryl acrylate with 25 mg of polymer. In the modified analysis procedure, isopropyl myristate standards did not contain copolymer. Unless otherwise indicated, each J-value is the average of three independent determinations.

TABLE 2

| Example Number | Copolymer Type | iv (dl/g) | Wt Percent IPM Calc. | Wt Percent IPM Actual | Wet Coating Thickness (mil/μM) | J-value (× 10⁻⁵ cm²/dyne) |
|---|---|---|---|---|---|---|
| 34 | 78/14/8 IOA/HEA/PSMac | 1.60[1] | 20 | 13.5 | 10/254 | 1.68[2] |
| 35 | 78/14/8 IOA/HEA/PSMac | 1.07[1] | 20 | 11.7 | 10/254 | 3.86 |
| 36 | 95/5 IOA/PSMac | 0.47 | 20 | 12.5 | 10/254 | 12.8 |
| 37 | 55/40/5 IOA/HEA/PSMac | 0.38 | 20 | 13.4 | 10/254 | 19.7 |
| 38 | 55/40/5 IOA/HEA/PMMAMac | 0.34 | 20 | 10.5 | 10/254 | 10.3 |

[1]Run in tetrahydrofuran
[2]Average of 4 determinations

EXAMPLE 39

Copolymer (50 g of 51/34/15 IOA/HEA/PSMac, 39.2% solids in 95/5 ethyl acetate/isopropanol, iv=0.73 dl/g) and oleyl alcohol (8.4 g) were combined in a glass jar. The jar was capped and placed on a roller for about 24 hours. The resulting formulation was knife coated at a wet thickness of 15 mil (381 µM) onto a silicone release liner [5 mil (127 µM) Daubert PESTER]. The coated release liner was oven dried at 110° F. (43° C.) for 20 minutes. The resulting coating theoretically contained 70 percent 51/34/15 IOA/HEA/PSMac copolymer and 30 percent oleyl alcohol. The coated liner was laminated to a backing (1109 SCOTCHPAK™ tan, polyester film laminate, available from the 3M Company). The compliance was measured using the test method described above and found to be 0.74×10$^{-5}$ cm$^2$/dyne (average of three independent determinations). A portion of the coating was removed from the backing and assayed for oleyl alcohol using the test method described above. The oleyl alcohol content was found to be 28 percent.

EXAMPLES 40–106

Using the general method of Example 39, a series of coated sheet materials in which the copolymer, softener and amount of softener were varied was prepared. The copolymer, identity and amount (weight percent, both calculated and determined using the methods described above) of softener, wet coating thickness, and the compliance values are shown in Table 3. Unless otherwise indicated, each J-value is the average of three independent determinations.

TABLE 3

| Example Number | Copolymer Type | iv (dl/g) | Softener ID | Softener Calc | Softener Actual | Wet Coating Thickness (mil/µM) | J-value (×10$^{-5}$ cm$^2$/dyne) |
|---|---|---|---|---|---|---|---|
| C3 | 57/38/5 IOA/HEA/PSMac | 0.65 | None | 0 | 0 | 15/381 | 0.92[1] |
| 40 | 57/38/5 IOA/HEA/PSMac | 0.65 | OA | 10 | 8.9 | 15/381 | 2.05 |
| 41 | 57/38/5 IOA/HEA/PSMac | 0.65 | OA | 20 | 19.9 | 15/381 | 3.39 |
| 42 | 57/38/5 IOA/HEA/PSMac | 0.65 | OA | 30 | 29.7 | 15/381 | 4.29 |
| C4 | 95/5 IOA/PSMac | 0.45 | none | 0 | 0 | 15/381 | 3.22 |
| 43 | 95/5 IOA/PSMac | 0.45 | OA | 20 | 18.9 | 15/381 | 5.00 |
| 44 | 95/5 IOA/PSMac | 0.45 | OA | 40 | 37.1 | 15/381 | 8.16 |
| C5 | 90/10 IOA/PSMac | 0.65 | none | 0 | 0 | 15/381 | 1.07 |
| 45 | 90/10 IOA/PSMac | 0.65 | OA | 20 | 18.8 | 15/381 | 1.63 |
| 46 | 90/10 IOA/PSMac | 0.65 | OA | 40 | 39 | 15/381 | 2.72 |
| C6 | 85/15 IOA/PSMac | 0.55 | none | 0 | 0 | 15/381 | 0.56 |
| 47 | 85/15 IOA/PSMac | 0.55 | OA | 20 | 19 | 15/381 | 0.85 |
| 48 | 85/15 IOA/PSMac | 0.55 | OA | 40 | 36 | 15/381 | 1.74 |
| 49 | 57/38/5 IOA/HEA/PSMac | 0.65 | OA | 40 | 37 | 15/381 | 4.99 |
| 50 | 57/38/5 IOA/HEA/PSMac | 0.65 | OA | 60 | 56.5 | 15/381 | 221[2] |
| 51 | 57/38/5 IOA/HEA/PSMac | 0.65 | OA | 60 | — | 4/102 | 1300[2] |
| 52 | 95/5 IOA/PSMac | 0.45 | OA | 40 | 36.7 | 15/381 | 9.88 |
| 53 | 95/5 IOA/PSMac | 0.45 | OA | 60 | 52.8 | 15/381 | not run |
| 54 | 95/5 IOA/PSMac | 0.45 | OA | 60 | — | 4/102 | not run |
| 55 | 90/10 IOA/PSMac | 0.65 | OA | 40 | 38 | 15/381 | 2.95 |
| 56 | 90/10 IOA/PSMac | 0.65 | OA | 60 | 56.6 | 15/381 | not run |
| 57 | 90/10 IOA/PSMac | 0.65 | OA | 60 | — | 4/102 | 4.12[1] |
| 58 | 85/15 IOA/PSMac | 0.55 | OA | 40 | 40.5 | 15/381 | 1.99 |
| 59 | 85/15 IOA/PSMac | 0.55 | OA | 60 | 60 | 15/381 | 48.2[2] |
| 60 | 85/15 IOA/PSMac | 0.55 | OA | 60 | — | 4/102 | 2.82[3] |
| C7 | 54/36/10 IOA/HEA/PSMac | 0.54 | none | 0 | 0 | 15/381 | 0.51 |
| 61 | 54/36/10 IOA/HEA/PSMac | 0.54 | OA | 10 | 9.1 | 15/381 | 0.83 |
| 62 | 54/36/10 IOA/HEA/PSMac | 0.54 | OA | 20 | 18.3 | 15/381 | 1.18 |
| 63 | 54/36/10 IOA/HEA/PSMac | 0.54 | OA | 30 | 28.1 | 15/381 | 1.63 |
| 64 | 54/36/10 IOA/HEA/PSMac | 0.54 | OA | 40 | 37.6 | 15/381 | 2.32 |
| 65 | 54/36/10 IOA/HEA/PSMac | 0.54 | OA | 60 | 56.9 | 15/381 | 190[2] |
| 66 | 54/36/10 IOA/HEA/PSMac | 0.54 | OA | 60 | — | 4/102 | 230[2] |
| 67 | 95/5 IOA/PSMac | 0.45 | OA | 47 | 45.5 | 15/381 | 40.5[2] |
| 68 | 90/10 IOA/PSMac | 0.65 | OA | 47 | 48 | 15/381 | 3.34 |
| 69 | 90/10 IOA/PSMac | 0.65 | OA | 53 | 53.5 | 15/381 | 6.26[3] |
| 70 | 90/10 IOA/PSMac | 0.65 | OA | 53 | — | 4/102 | 4.43[2] |
| 71 | 85/15 IOA/PSMac | 0.55 | OA | 47 | 42.2 | 15/381 | 15.1[3] |
| 72 | 85/15 IOA/PSMac | 0.55 | OA | 53 | 50.7 | 15/381 | 27.0[3] |
| 73 | 57/38/5 IOA/HEA/PMMAMac* | 0.53 | IPM | 20 | 19.2 | 15/381 | 2.34[3] |
| 74 | 57/38/5 IOA/HEA/PMMAMac* | 0.53 | IPM | 40 | 39.3 | 15/381 | 34.4 |
| 75 | 54/36/10 IOA/HEA/PMMAMac* | 0.46 | IPM | 20 | 19.6 | 15/381 | 0.79 |
| 76 | 54/36/10 IOA/HEA/PMMAMac* | 0.46 | IPM | 40 | 38.5 | 15/381 | 93.3[2] |
| C8 | 51/34/15 IOA/HEA/PMMAMac* | 0.35 | None | 0 | 0 | 15/381 | 0.42 |
| 77 | 51/34/15 IOA/HEA/PMMAMac* | 0.35 | IPM | 10 | 9.6 | 15/381 | 0.83[3] |
| 78 | 51/34/15 IOA/HEA/PMMAMac* | 0.35 | IPM | 20 | 18.7 | 15/381 | 1.18[3] |
| 79 | 51/34/15 IOA/HEA/PMMAMac* | 0.35 | IPM | 30 | 27.2 | 15/381 | 1.52[3] |
| 80 | 51/34/15 IOA/HEA/PMMAMac* | 0.35 | LPM | 40 | 36.6 | 15/381 | 334[2] |
| 81 | 5I/34/15 IOA/HEA/PMMAMac* | 0.35 | LPM | 50 | 42.1 | 4/102 | 4.46[3] |
| 82 | 51/34/15 IOA/HEA/PMMAMac* | 0.35 | IPM | 60 | 45.2 | 4/102 | 4.26[3] |
| 83 | 51/34/15 IOA/HEA/PMMAMac* | 0.35 | OA | 10 | 9.7 | 15/381 | 0.61[3] |
| 84 | 51/34/15 IOA/HEA/PMMAMac* | 0.35 | OA | 20 | 19.3 | 15/381 | 0.94[3] |
| 85 | 51/34/15 IOA/HEA/PMMAMac* | 0.35 | OA | 30 | 30.5 | 15/381 | 1.22[3] |
| 86 | 51/34/15 IOA/HEA/PMMAMac* | 0.35 | OA | 40 | 40.3 | 15/381 | 1.77[3] |
| 87 | 51/34/15 IOA/HEAIPMMAMac* | 0.35 | OA | 50 | 48.7 | 15/381 | 2.43[3] |
| 88 | 51/34/15 IOA/HEA/PMMAMac* | 0.35 | OA | 60 | 58.6 | 15/381 | 3.69[3] |
| 89 | 51/34/15 IOA/HEAIPMMAMac* | 0.35 | OA | 60 | 60.1 | 4/102 | 4.03[2] |

TABLE 3-continued

| Example Number | Copolymer Type | iv (dl/g) | Softener ID | Softener Calc | Softener Actual | Wet Coating Thickness (mil/μM) | J-value (×10⁻⁵ cm²/dyne) |
|---|---|---|---|---|---|---|---|
| 90 | 57/38/5 IOA/HEA/PSMac | 0.65 | OA | 47 | 46.3 | 15/381 | 9.86 |
| 91 | 57/38/5 IOA/HEA/PSMac | 0.65 | OA | 47 | — | 4/102 | 36.3³ |
| 92 | 57/38/5 IOA/HEAIPSMac | 0.65 | OA | 53 | 52.3 | 15/381 | 47.2 |
| 93 | 57/38/5 IOA/HEA/PSMac | 0.65 | OA | 53 | — | 4/102 | 2.87² |
| 94 | 54/36/10 IOA/HEA/PSMac | 0.56 | OA | 47 | 46 | 15/381 | 2.99 |
| 95 | 54/36/10 IOA/HEA/PSMac | 0.56 | OA | 47 | — | 4/102 | 3.62³ |
| 96 | 54/36/10 IOA/HEA/PSMac | 0.56 | OA | 53 | 51 | 15/381 | 19.1 |
| 97 | 54/36/10 IOA/HEA/PSMac | 0.56 | OA | 53 | — | 4/102 | 125³ |
| C9 | 51/34/15 IOA/HEA/PSMac | 0.52 | none | 0 | 0 | 15/381 | 0.36 |
| 98 | 51/34/15 IOA/HEA/PSMac | 0.52 | OA | 10 | 10 | 15/381 | 0.50 |
| 99 | 51/34/15 IOA/HEA/PSMac | 0.52 | OA | 20 | 19.7 | 15/381 | 0.56 |
| 100 | 51/34/15 IOA/HEA/PSMac | 0.52 | OA | 30 | 30.4 | 15/381 | 0.77³ |
| 101 | 51/34/15 IOA/HEA/PSMac | 0.52 | OA | 40 | 40.5 | 15/381 | 1.16 |
| 102 | 51/34/15 IOA/HEA/PSMac | 0.52 | OA | 47 | 48.1 | 15/381 | 1.56 |
| 103 | 51/34/15 IOA/HEA/PSMac | 0.52 | OA | 47 | — | 4/102 | 1.81³ |
| 104 | 51/34/15 IOA/HEA/PSMac | 0.52 | OA | 53 | 53.9 | 15/381 | 33.7 |
| 105 | 51/34/15 IOA/HEA/PSMac | 0.52 | OA | 53 | — | 4/102 | 4.04² |
| 106 | 51/34/15 IOA/HEA/PSMac | 0.52 | OA | 60 | 61 | 15/381 | 147² |

[1]Average of four determinations
[2]Single determination
[3]Average of two determinations
PMMAMac* is ELVACITE 1020

EXAMPLES 107–129

Using the general method of Example 39, a series of coated sheet materials in which the copolymer, softener and amount of softener were varied was prepared. The copolymer, identity and amount (weight percent) of softener, wet coating thickness, and the compliance values are shown in Table 4. Unless otherwise indicated, each J-value is the average of two independent determinations. When the compliance was "not run", the formulation was too soft to be tested.

TABLE 4

| Example Number | Copolymer Type | iv (dl/g) | Softener | Wet Coating Thickness (mil/μM) | J-value (×10⁻⁵ cm²/dyne) |
|---|---|---|---|---|---|
| C10 | 57/38/5 IOA/HEA/PMMAMac* | 0.54 | none | 15/381 | 0.80¹ |
| 107 | 57/38/5 IOA/HEA/PMMAMac* | 0.54 | 10% IPM⁴ | 15/381 | 1.50 |
| 108 | 57/38/5 IOA/HEA/PMMAMac* | 0.54 | 20% IPM⁴ | 15/381 | 2.62 |
| 109 | 57/38/5 IOA/HEA/PMMAMac* | 0.54 | 30% IPM⁴ | 15/381 | 4.58 |
| 110 | 57/38/5 IOA/HEA/PMMAMac* | 0.54 | 40% IPM⁴ | 4/102 | 64.2² |
| 111 | 57/38/5 IOAIHEA/PMMAMac* | 0.54 | 50% IPM | 4/102 | not run |
| 112 | 57/38/15 IOA/HEA/PMMAMac* | 0.54 | 60% IPM | 4/102 | not run |
| C11 | 54/36/10 IOA/HEA/PMMAMac* | 0.50 | none | 15/381 | 0.44 |
| 113 | 54/36/10 IOA/HEA/PMMAMac* | 0.50 | 10% IPM⁴ | 15/381 | 0.69 |
| 114 | 54/36/IO IOA/HEA/PMMAMac* | 0.50 | 20% IPM⁴ | 15/381 | 0.94³ |
| 115 | 54/36/10 IOA/HEA/PMMAMac* | 0.50 | 30% IPM⁴ | 15/381 | 1.46 |
| 116 | 54/36/10 IOA/HEA/PMMAMac* | 0.50 | 40% IPM | 4/102 | not run |
| 117 | 54/36/10 IOA/HEA/PMMAMac* | 0.50 | 50% IPM | 4/102 | not run |
| 118 | 57/38/5 IOA/HEA/PMMAMac* | 0.54 | 10% OA | 15/381 | 1.63 |
| 119 | 57/38/5 IOA/HEA/PMMAMac* | 0.54 | 20% OA | 15/381 | 2.70 |
| 120 | 57/38/5 IOA/HEA/PMMAMac* | 0.54 | 30% OA | 15/381 | 4.19 |
| 121 | 57/38/5 IOA/HEA/PMMAMac* | 0.54 | 40% OA | 4/102 | 6.01 |
| 122 | 57/38/5 IOA/HEA/PMMAMac* | 0.54 | 50% OA | 4/102 | 8.27 |
| 123 | 57/3815 IOA/HEAIPMMAMac* | 0.54 | 60% OA | 4/102 | 11.8 |
| 124 | 54/36/10 IOA/HEA/PMMAMac* | 0.50 | 10% OA | 15/381 | 0.60 |
| 125 | 54/36/10 IOA/HEA/PMMAMac* | 0.50 | 20% OA | 15/381 | 0.89 |
| 126 | 54/36/10 IOAIHEA/PMMAMac* | 0.50 | 30% OA | 15/381 | 1.19 |
| 127 | 54/36/10 IOAIHEA/PMMAMac* | 0.50 | 40% OA | 4/102 | 1.56 |
| 128 | 54/36/10 IOA/HEA/PMMAMac* | 0.50 | 50% OA | 4/102 | 2.65 |
| 129 | 54/36/10 IOA/HEA/PMMAMac* | 0.50 | 60% OA | 4/102 | 3.99 |

PMMAMac* is ELVACITE 1020
[1]Average of four determinations
[2]Single determination
[3]Average of three determinations
[4]IPM content confirmed using the test method described above.

EXAMPLE 130

Copolymer (6.7306 g of 63/27/10 IOA/IDMACM/PMMAMac, 47.8% solids in 95/5 w/w ethyl acetate/isopropanol, iv=0.39 dl/g), levonorgestrel (0.0502 g) and methyl laurate (1.7606 g) were combined in an 11 dram (40.7 mL) glass vial. The vial was capped then shaken overnight on a platform shaker. The resulting formulation was knife coated at a thickness of 16 mil (406 μm) onto a release liner (Daubert 164Z 5 mil [127 μM] PESTER). The coated release liner was oven dried for 4 minutes at 125° F. (52° C.), for 2 minutes at 185° F. (85° C.) and for 2 mi 225° F. (107° C.). The resulting adhesive coating contained 64.0 percent 63/27/10 IOA/HEA/PMMAMac copolymer, 1.0 percent levonorgestrel and 35.0 percent methyl laurate. The coated liner was then laminated onto the corona treated surface of a 3 mil (76.2 μm) polyethylene backing. The compliance was measured using the test method described above and found to be $4.4 \times 10^{-5}$ cm$^2$/dyne.

EXAMPLES 131–178

Using the general method of Example 130, a number of coated sheet materials were prepared in order to assess the effect of increasing the amount of skin penetration enhancer (s) on the compliance of certain formulations containing levonorgestrel. The compliance was measured using the test method described above. The formulations and the J-values are shown in Table 5, where amounts are percent by weight. Except as noted, the polymethylmethacrylate macromonomer was ELVACITE 1010. PMMAMac* indicates that the polymethylmethacrylate was ELVACITE 1020.

TABLE 5

| Ex No. | Adhesive Amount | Adhesive Type | iv | GM LN | DDA L | O | Additional Enhancer(s) | J-Value (cm$^2$/dyne) |
|---|---|---|---|---|---|---|---|---|
| 131 | 68.7 | 63/27/10 IOA/DMACM/PMMAMac | | 1.0 | 0 | 0 | 30.3 ML | $2.4 \times 10^{-5}$ |
| 132 | 74.2 | 63/27/10 IOA/DMACM/PMMAMac | | 1.0 | 0 | 0 | 24.8 ML | $2.1 \times 10^{-5}$ |
| 133 | 64.5 | 55/40/5 IOA/HEA/PMMAMac | | 1.0 | 0 | 0 | 17.1 DGME 17.4 LG | off scale |
| 134 | 68.7 | 55/40/5 IOA/HEA/PMMAMac | | 1.0 | 0 | 0 | 15.2 DGME 15.1 LG | $15.4 \times 10^{-5}$ |
| 135 | 74.0 | 55/40/5 IOA/HEA/PMMAMac | | 1.0 | 0 | 0 | 12.6 DGME 12.4 LG | $5.2 \times 10^{-5}$ |
| 136 | 78.9 | 55/40/5 IOA/HEA/PMMAMac | | 1.0 | 0 | 0 | 10.1 DGME 10.0 LG | $5.0 \times 10^{-5}$ |
| 137 | 65.7 | 55/40/5 IOA/HEA/PMMAMac | 0.51 | 1.0 | 5.0 | 3.0 | 12.8 DGME 12.5 LG | $2.6 \times 10^{-5}$ |
| 138 | 60.9 | 55/40/5 IOA/HEA/PMMAMac | 0.51 | 1.0 | 5.0 | 3.0 | 15.0 DGME 15.1 LG | $2.9 \times 10^{-5}$ |
| 139 | 55.8 | 55/40/5 IOA/HEA/PMMAMac | 0.51 | 1.0 | 5.0 | 3.0 | 17.6 DGME 17.6 LG | $3.4 \times 10^{-5}$ |
| 140 | 51.1 | 55/40/5 IOA/HEA/PMMAMac | 0.51 | 1.0 | 5.0 | 3.0 | 20.0 DGME 19.9 LG | $8.1 \times 10^{-5}$ |
| 141 | 65.4 | 55/35/10 IOA/HEA/PMMAMac | 0.42 | 1.0 | 4.9 | 3.1 | 12.7 DGME 12.9 LG | $2.2 \times 10^{-5}$ |
| 142 | 60.5 | 55/35/10 IOA/HEA/PMMAMac | 0.42 | 1.0 | 4.9 | 3.0 | 15.4 DGME 15.2 LG | $1.9 \times 10^{-5}$ |
| 143 | 55.7 | 55/35/10 IOA/HEA/PMMAMac | 0.42 | 1.0 | 5.2 | 3.0 | 17.6 DGME 17.5 LG | $2.2 \times 10^{-5}$ |
| 144 | 50.7 | 55/35/10 IOA/HEA/PMMAMac | 0.42 | 1.1 | 5.0 | 2.9 | 20.0 DGME 20.3 LG | $2.8 \times 10^{-5}$ |
| 145 | 65.4 | 55/35/10 IOA/HEA/PMMAMac* | 0.46 | 1.0 | 4.9 | 3.0 | 13.1 DGME 12.6 LG | $1.5 \times 10^{-5}$ |
| 146 | 60.7 | 55/35/10 IOA/HEA/PMMAMac* | 0.46 | 1.1 | 5.4 | 3.0 | 15.0 DGME 14.8 LG | $1.8 \times 10^{-5}$ |
| 147 | 56.0 | 55/35/10 IOA/HEA/PMMAMac* | 0.46 | 1.0 | 5.0 | 3.0 | 17.5 DGME 17.5 LG | $2.2 \times 10^{-5}$ |
| 148 | 50.7 | 55/35/10 IOA/HEA/PMMAMac* | 0.46 | 1.1 | 5.0 | 3.0 | 20.0 DGME 20.2 LG | $2.4 \times 10^{-5}$ |
| 149 | 52.9 | 63/27/10 IOA/DMACM/PMMAMac | 0.48 | 1.0 | 5.1 | 1.0 | 40.0 ML | $17.4 \times 10^{-5}$ |
| 150 | 58.0 | 63/27/10 IOA/DMACM/PMMAMac | 0.48 | 1.0 | 5.1 | 1.0 | 34.9 ML | $9.5 \times 10^{-5}$ |
| 151 | 63.1 | 63/27/10 IOA/DMACM/PMMAMac | 0.48 | 1.0 | 5.0 | 1.0 | 29.9 ML | $4.0 \times 10^{-5}$ |
| 152 | 67.8 | 63/27/10 IOA/DMACM/PMMAMac | 0.48 | 1.0 | 5.1 | 1.1 | 25.0 ML | $3.7 \times 10^{-5}$ |
| 153 | 72.9 | 63/27/10 IOA/DMACM/PMMAMac | 0.48 | 1.0 | 5.0 | 1.0 | 20.1 ML | $2.2 \times 10^{-5}$ |
| 154 | 70.6 | 55/40/5 IOA/HEA/PMMAMac | 0.51 | 1.0 | 5.0 | 3.0 | 10.3 PG 10.1 ML | $3.3 \times 10^{-5}$ |
| 155 | 65.0 | 55/40/5 IOA/HEA/PMMAMac | 0.51 | 1.0 | 5.1 | 3.0 | 12.3 PG 13.6 ML | $3.1 \times 10^{-5}$ |
| 156 | 60.5 | 55/40/5 IOA/HEA/PMMAMac | 0.51 | 1.0 | 5.0 | 3.1 | 15.3 PG 15.1 ML | $4.9 \times 10^{-5}$ |
| 157 | 55.7 | 55/40/5 IOA/HEA/PMMAMac | 0.51 | 1.0 | 5.1 | 3.0 | 17.7 PG 17.5 ML | $5.3 \times 10^{-5}$ |

TABLE 5-continued

| Ex No. | Adhesive Amount | Adhesive Type | iv | GM LN | L | DDA O | Additional Enhancer(s) | J-Value (cm²/dyne) |
|---|---|---|---|---|---|---|---|---|
| 158 | 51.0 | 55/40/5 IOA/HEA/PMMAMac | 0.51 | 1.0 | 5.0 | 3.0 | 20.2 PG 19.8 ML | 3.4 × 10⁻⁵ |
| 159 | 69.8 | 55/35/10 IOA/HEA/PMMAMac | 0.42 | 1.0 | 5.2 | 3.0 | 10.0 PG 11.0 ML | 1.4 × 10⁻⁵ |
| 160 | 66.1 | 55/35/10 IOA/HEA/PMMAMac | 0.42 | 1.0 | 4.9 | 3.0 | 12.3 PG 12.7 ML | 1.4 × 10⁻⁵ |
| 161 | 60.7 | 55/35/10 IOA/HEA/PMMAMac | 0.42 | 1.0 | 5.0 | 3.0 | 15.3 PG 15.0 ML | 2.0 × 10⁻⁵ |
| 162 | 55.8 | 55/35/10 IOA/HEA/PMMAMac | 0.42 | 1.0 | 5.0 | 3.0 | 17.7 PG 17.5 ML | 2.3 × 10⁻⁵ |
| 163 | 50.7 | 55/35/10 IOA/HEA/PMMAMac | 0.42 | 1.0 | 5.3 | 3.0 | 20.2 PG 19.8 ML | 2.7 × 10⁻⁵ |
| 164 | 72.0 | 60/15/15/10 IOA/DMACM/HEA/PMMAMac | 0.47 | 1.0 | 5.0 | 2.0 | 14.3 ML 5.7 DIPA | 2.0 × 10⁻⁵ |
| 165 | 67.3 | 60/15/15/10 IOA/DMACM/HEA/PMMAMac | 0.47 | 1.0 | 5.0 | 2.1 | 17.8 ML 6.8 DIPA | 2.4 × 10⁻⁵ |
| 166 | 61.7 | 60/15/15/10 IOA/DMACM/HEA/PMMAMac | 0.47 | 1.0 | 5.0 | 2.1 | 21.8 ML 8.4 DIPA | 5.0 × 10⁻⁵ |
| 167 | 56.9 | 60/15/15/10 IOA/DMACM/HEA/PMMAMac | 0.47 | 1.0 | 5.1 | 2.0 | 25.4 ML 9.6 DIPA | 7.8 × 10⁻⁵ |
| 168 | 52.0 | 60/15/15/10 IOA/DMACM/HEA/PMMAMac | 0.47 | 1.0 | 5.2 | 2.0 | 28.8 ML 11.0 DIPA | 16.6 × 10⁻⁵ |
| 169 | 72.7 | 68/27/5 IOA/DMACM/PMMAMac | 0.47 | 1.0 | 5.0 | 1.0 | 20.3 ML | 15.4 × 10⁻⁵ |
| 170 | 68.0 | 68/27/5 IOA/DMACM/PMMAMac | 0.47 | 1.0 | 5.0 | 1.1 | 24.9 ML | 24.8 × 10⁻⁵ |
| 171 | 72.2 | 50/40/10 IOA/DMACM/PMMAMac | 0.53 | 1.0 | 4.9 | 1.0 | 20.9 ML | 1.8 × 10⁻⁵ |
| 172 | 67.7 | 50/40/10 IOA/DMACM/PMMAMac | 0.53 | 1.0 | 5.0 | 1.0 | 25.3 ML | 2.7 × 10⁻⁵ |
| 173 | 63.5 | 50/40/10 IOA/DMACM/PMMAMac | 0.53 | 1.0 | 4.9 | 1.0 | 29.6 ML | 5.2 × 10⁻⁵ |
| 174 | 58.3 | 50/40/10 IOA/DMACM/PMMAMac | 0.53 | 1.0 | 5.0 | 1.1 | 34.5 ML | 10.7 × 10⁻⁵ |
| 175 | 53.0 | 50/40/10 IOA/DMACM/PMMAMac | 0.53 | 1.0 | 5.1 | 1.1 | 39.8 ML | 21.5 × 10⁻⁵ |
| 176 | 71.0 | 65/15/15/5 IOA/DMACM/HEA/PMMAMac | 0.47 | 1.0 | 5.0 | 2.0 | 13.7 ML 7.3 DIPA | 8.8 × 10⁻⁵ |
| 177 | 66.7 | 65/15/15/5 IOA/DMACM/HEA/PMMAMac | 0.47 | 1.0 | 5.1 | 2.0 | 17.5 ML 7.3 DIPA | 13.2 × 10⁻⁵ |
| 178 | 62.6 | 65/15/15/5 IOA/DMACM/HEA/PMMAMac | 0.47 | 1.0 | 5.1 | 2.0 | 20.3 ML 9.0 DIPA | 22.9 × 10⁻⁵ |

In Vitro Skin Penetration Test Method

The skin penetration data given in the examples below was obtained using the following test method. A Diffusion cell is used. Human cadaver skin (Dermatomed skin about 500 μM thick obtained from a skin bank) is used. The skin 22 is mounted epidermal side up between upper portion 24 and lower portion 26 of the cell, which are held together by means of ball joint clamp 28.

The portion of the cell below the mounted skin is completely filled with receptor fluid (30% N-methyl-2-pyrrolidone in water) such that the receptor fluid is in contact with the skin. The receptor fluid is stirred using a magnetic stirrer (not illustrated). The sampling port 30 is covered except when in use.

When a transdermal delivery device is evaluated, the skin is placed across the orifice of the lower portion of the diffusion cell, the release liner is removed from a 2.0 cm² patch and the patch is applied to the skin and pressed to cause uniform contact with the skin. The diffusion cell is assembled and the lower portion is filled with 10 mL of warm (32° C.) receptor fluid.

The cell is the placed in a constant temperature (32±2° C.) and humidity (50±10% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals (6, 12, 24, 48 and 72 hours) and immediately replaced with fresh fluid. The withdrawn fluid is filtered through a 0.45 μM filter. A 1 mL portion of filtrate is then analyzed for levonorgestrel using high performance liquid chromatography (Column: 15 cm X 4.6 mm I.D. ZORBAX™ RX-C 18 from DuPont, 5 μM particle size; Mobile Phase: 60/40 v/v water/acetonitrile; Flow Rate: 1.5 mL/min; Run Time: 11.0 min; Detection: uv at 230 nm). The cumulative amount of levonorgestrel penetrating the skin is calculated. The greatest slope of a plot of the cumulative penetration versus time is reported as steady state levonorgestrel flux measured in μg/cm²/hour.

EXAMPLE 179

Levonorgestrel (19.85 g), methyl laurate (330.8 g), propylene glycol (198.5 g), glyceryl monolaurate (33.08 g), N,N-dimethyldodecylamine-N-oxide (19.85 g) and copolymer (1803 g of 55/40/5 IOA/HEA/PMMAMac copolymer, 40% solids in 95/5 w/w ethyl acetate/isopropanol, which had been dried then resolvated, iv=0.59 dl/g after drying) were placed in a 1 gallon (3.8 L) high density polyethylene carboy. The carboy was tightly capped then placed on a roller/shaker for 19 hours. The carboy was allowed to stand until all entrapped air bubbles had dissipated. The resulting formulation was knife coated at a wet thickness of 16 mil (406 µM) onto a silicone coated polyester (5 mil, 127 µM) film. The coated release liner was oven dried at 127° F. (53° C.) for 30 minutes. The resulting adhesive coating contained 1.5 percent levonorgestrel, 15.0 percent propylene glycol, 25.0 percent methyl laurate, 2.5 percent glyceryl monolaurate, 1.5 percent N,N-dimethyldodecylamine-N-oxide, and 54.5 percent 55/40/5 IOA/HEA/PMMAMac copolymer. The coated liner was allowed to cool for 10 minutes then it was laminated to the corona treated side of a 2 mil (51 µM) polypropylene film. The compliance was measured using the test method described above and found to be $6.57 \times 10^{-5}$ cm$^2$/dynes. Skin penetration through human cadaver skin was measured using the test method described above; the steady state flux was found to be 0.166 µg/cm$^2$/hr.

EXAMPLE 180

Levonorgestrel (18.29 g), methyl laurate (457.2 g), glyceryl monolaurate (65.31 g), N,N- dimethyldodecylamine-N-oxide (13.06 g) and copolymer (1401 g of 50/40/10 IOA/DMACM/PMMAMac copolymer, 53.7% solids in 95/5 w/w ethyl acetate/isopropanol, which had been dried then resolvated, iv=0.55 dl/g before drying; iv=0.52 dl/g after drying) were placed in a 1 gallon (3.8 L) high density polyethylene carboy. The carboy was tightly capped then placed on a roller/shaker for 19 hours. The carboy was allowed to stand until all entrapped air bubbles had dissipated. The resulting formulation was knife coated at a wet thickness of 12 mil (305 µM) onto a silicone coated polyester (5 mil, 127 µM) film. The coated release liner was oven dried at 127° F. (53° C.) for 80 minutes. The resulting adhesive coating contained 1.4 percent levonorgestrel, 35.0 percent methyl laurate, 5.0 percent glyceryl monolaurate, 1.0 percent N,N-dimethyldodecylamine-N-oxide, and 57.6 percent 50/40/10 IOA/DMACM/PMMAMac copolymer. The coated liner was allowed to cool for 10 minutes then it was laminated to the corona treated side of a 2 mil (51 µM) polypropylene film. The compliance was measured using the test method described above and found to be $5.74 \times 10^{-5}$ cm$^2$/dynes. Skin penetration through human cadaver skin was measured using the test method described above; the steady state flux was found to be 0.148 µg/cm$^2$/hr.

EXAMPLE 181

Levonorgestrel (18.04 g), methyl laurate (264.6 g), tetraglycol (96.23 g), glyceryl monolaurate (60.14 g), N,N-dimethyldodecylamine-N-oxide (12.03 g) and copolymer (1400 g of 50/40/10 IOA/DMACM/PMMAMac copolymer, 53.7% solids in 95/5 w/w ethyl acetate/isopropanol, which had been dried then resolvated, iv=0.55 dl/g before drying; iv=0.52 dl/g after drying) were placed in a 1 gallon (3.8 L) high density polyethylene carboy. The carboy was tightly capped then placed on a roller/shaker for 19 hours. The carboy was allowed to stand until all entrapped air bubbles had dissipated. The resulting formulation was knife coated at a wet thickness of 13 mil (330 µM) onto a silicone coated polyester (5 mil, 127 µM) film. The coated release liner was oven dried at 127° F. (53° C.) for 75 minutes. The resulting adhesive coating contained 1.5 percent levonorgestrel, 22.0 percent methyl laurate, 8.0 percent tetraglycol, 5.0 percent glyceryl monolaurate, 1.0 percent N,N-dimethyldodecylamine-N-oxide, and 62.5 percent 50/40/10 IOA/DMACM/PMMAMac copolymer. The coated liner was allowed to cool for 10 minutes then it was laminated to the corona treated side of a 2 mil (51 µM) polypropylene film. The compliance was measured using the test method described above and found to be $8.72 \times 10^{-5}$ cm$^2$/dynes. Skin penetration through human cadaver skin was measured using the test method described above; the steady state flux was found to be 0.131 µg/cm$^2$/hr.

EXAMPLE 182

Copolymer (50.13 g of 57/38/5 IOA/HEA/PMMAMac, 39.5% solids in 97/3 ethyl acetate/isopropanol, iv=0.69 dl/g) and nicotine (5.04 g) were combined in a glass jar. The jar was capped and shaken for 15 minutes. The resulting formulation was knife coated at a wet thickness of 8 mil (203 µM) onto a silicone coated polyester release liner (5 mil (127 µM) Daubert). The coated release liner was oven dried at 110° F. (43° C.) for 30 minutes. The resulting coating theoretically contained 79.71 percent 57/38/5 IOA/HEA/PMMAMac copolymer and 20.29 percent nicotine. The coated liner was laminated to a backing (1109 SCOTCH-PAK™ tan, polyester film laminate, available from the 3M Company). The compliance was measured 4 hours after the laminate was prepared using the test method described above and found to be $1.79 \times 10^{-5}$ cm$^2$/dyne. The compliance was measured again after the laminate had sat overnight and was found to be $1.5 \times 10^{-5}$ cm$^2$/dyne (average of two independent determinations).

EXAMPLE 183

The formulation prepared in Example 182 was knife coated at a wet thickness of 6 mil (152 µM) onto a silicone coated polyester release liner (5 mil (127 µM) Daubert). The coated release liner was allowed to dry at ambient temperature (22° C.) for 100 minutes. The resulting coating theoretically contained 79.71 percent 57/38/5 IOA/HEA/PMMAMac copolymer and 20.29 percent nicotine. The coated liner was laminated to a backing (1109 SCOTCH-PAK™ tan, polyester film laminate, available from the 3M Company). The compliance was measured after the laminate had sat over the weekend and was found to be $2.4 \times 10^{-5}$ cm$^2$/dyne (average of two determinations).

EXAMPLE 184

Copolymer (10.0 g of 55/9/28/8 2-ethylhexylacrylate/vinyl acetate/tetrahydrofrfuryl acrylate/ELVACITE 1020 PMMAMac 37.28% solids in 90/10 w/w ethyl acetate/isopropanol, iv=0.706 dl/g) and isopropyl myristate (0.93 g) were combined then mixed to provide a homogeneous formulation. The formulation was coated at a wet thickness of 15 mil (381 µM) onto a polyethylene terephthalate film then air dried to provide a pressure sensitive adhesive with clean release from skin.

EXAMPLE 185

Copolymer (10.0 g of 55/9/28/8 2-ethylhexylacrylate/vinyl acetate/tetrahydrofurfuryl acrylate/ELVACITE 1020 PMMAMac 37.28% solids in 90/10 w/w ethyl acetate/isopropanol, 0.706 dl/g) and isopropyl myristate (1.60 g) were combined then mixed to provide a homogeneous formulation. The formulation was coated at a wet thickness of 15 mil (381 ∞M) onto a polyethylene terephthalate film then air dried to provide a pressure sensitive adhesive with clean release from skin.

EXAMPLE 186

Copolymer (10.0 g of 82/10/8 IOA/2-hydroxyethyl methacrylate/ELVACITE 1020 PMMAMac 38.7% solids in 95/5 w/w ethyl acetate/isopropanol, iv=0.378 dl/g) and oleyl alcohol (0.97 g) were combined then mixed to provide a homogeneous formulation. The formulation was coated at a wet thickness of 15 mil (381 μM) onto a polyethylene terephthalate film then air dried to provide a pressure sensitive adhesive with clean release from skin.

EXAMPLE 187

Copolymer (10.0 g of 77/4/15/4 IOA/acrylamide/DMACM/ELVACITE 1020 PMMAMac 39.5% solids in 95/5 w/w ethyl acetate/isopropanol, iv=0.443 dl/g) and isopropyl myristate (0.99 g) were combined then mixed to provide a homogeneous formulation. The formulation was coated at a wet thickness of 15 mil (381 μM) onto a polyethylene terephthalate film then air dried to provide an aggressive pressure sensitive adhesive with clean release from skin.

EXAMPLE 188

Copolymer (10.0 g of 74/9/9/8 2-ethylhexyl acrylate/N-vinyl pyrrolidone/ 2-hydroxyethyl acrylate/ELVACITE 1020 PMMAMac 39.4% solids in 95/5 w/w ethyl acetate/isopropanol, iv=0.365 dl/g) and isopropyl myristate (0.99 g) were combined then mixed to provide a homogeneous formulation. The formulation was coated at a wet thickness of 15 mil (381 μM) onto a polyethylene terephthalate film then air dried to provide an aggressive pressure sensitive adhesive with clean release from skin.

EXAMPLE 189

Copolymer (10.0 g of 55/9/28/8 IOA/butyl methacrylate/ethoxy ethoxy ethyl acrylate/ELVACITE 1020 PMMAMac 38.3% solids in 95/5 w/w ethyl acetate/isopropanol, iv=0.78 dl/g) and oleyl alcohol (0.96 g) were combined then mixed to provide a homogeneous formulation. The formulation was coated at a wet thickness of 15 mil (381 μM) onto a polyethylene terephthalate film then air dried to provide a pressure sensitive adhesive with clean release from skin.

EXAMPLE 190

Copolymer (10.0 g of 55/9/28/8 IOA/butyl methacrylate/ethoxy ethoxy ethyl acrylate/ELVACITE 1020 PMMAMac 38.3% solids in 95/5 w/w ethyl acetate/isopropanol, iv=0.78 dl/g) and oleyl alcohol (1.64 g) were combined then mixed to provide a homogeneous formulation. The formulation was coated at a wet thickness of 15 mil (381 μM) onto a polyethylene terephthalate film then air dried to provide a pressure sensitive adhesive with limited tack and with clean release from skin.

EXAMPLE 191

Copolymer (10.0 g of 55/9/28/8 IOA/butyl acrylate/ethoxy ethoxy ethyl acrylate/ELVACITE 1020 PMMAMac 38.5% solids in 95/5 w/w ethyl acetate/isopropanol, iv=0.78 dl/g) and oleyl alcohol (0.96 g) were combined then mixed to provide a homogeneous formulation. The formulation was coated at a wet thickness of 15 mil (381 μM) onto a polyethylene terephthalate film then air dried to provide a pressure sensitive adhesive with clean release from skin.

EXAMPLE 192

Copolymer (10.0 g of 55/9/28/8 IOA/butyl acrylate/ethoxy ethoxy ethyl acrylate/ELVACITE 1020 PMMAMac 38.5% solids in 95/5 w/w ethyl acetate/isopropanol, iv=0.78 dl/g) and oleyl alcohol (1.65 g) were combined then mixed to provide a homogeneous formulation. The formulation was coated at a wet thickness of 15 mil (381 μM) onto a polyethylene terephthalate film then air dried to provide a pressure sensitive adhesive with limited tack and with clean release from skin.

EXAMPLE 193

Copolymer (100 g of 61/37/2 IOA/IVoAc/PSMac, 34 percent solids in 84/16 ethyl acetate/toluene, iv=0.87 dl/g) and oleyl alcohol (14.57 g) were combined in a glass jar. The jar was placed on a roller mixer overnight. The resulting formulation was knife coated at a wet thickness of about 7 mil (178 μM) onto a 2 mil (51 μM) polyethylene terephthalate film. The coated film was oven dried at 110° F. (43° C.) for 20 minutes. The resulting coating theoretically contained 70 percent 61/37/2 IOA/VoAc/PSMac copolymer and 30 percent oleyl alcohol. The coated film was folded back onto itself to form a "sandwich" and the compliance was measured using the test method described above. The compliance was found to be $6.8 \times 10^{-5}$ cm$^2$/dyne (average of three independent determinations).

EXAMPLE 194–218

Using the general method of Example 193, a series of coated sheet materials in which the copolymer, softener and amount of softener were varied was prepared. The copolymer, identity and amount (weight percent) of softener, and the compliance values are shown in Table 6 where each J-value is the average of three independent determinations. The polymethylmethacrylate macromonomer used was ELVACITE 1020.

TABLE 6

| Example Number | Copolymer Type | iv (dl/g) | Softener | J-value (X $10^{-5}$ cm$^2$/dyne) |
|---|---|---|---|---|
| C12 | 61/37/2 IOA/VoAc/PSMac | 0.87 | none | 1 |
| 194 | 61/37/2 IOA/VoAc/PSMac | 0.87 | 20% IPM | 15.7 |
| 195 | 61/37/2 IOA/VoAc/PSMac | 0.87 | 30% IPM | >20 |
| 196 | 61/37/2 IOA/VoAc/PSMac | 0.87 | 40% IPM | >20 |
| 197 | 61/37/2 IOA/VoAc/PSMac | 0.87 | 40% OA | >20 |
| C13 | 61/37/2 IOA/VoAc/PSMac | 0.87 | none | 0.65 |
| 198 | 61/37/2 IOA/VoAc/PSMac | 1.02 | 20% IPM | 8.3 |
| 199 | 61/37/2 IOA/VoAc/PSMac | 1.02 | 30% IPM | 17.6 |
| 200 | 61/37/2 IOA/VoAc/PSMac | 1.02 | 40% IPM | >20 |
| 201 | 61/37/2 IOA/VoAc/PSMac | 1.02 | 30% OA | 3.2 |

TABLE 6-continued

| Example Number | Copolymer Type | iv (dl/g) | Softener | J-value (X $10^{-5}$ cm$^2$/dyne) |
|---|---|---|---|---|
| 202 | 61/37/2 IOA/VoAc/PSMac | 1.02 | 40% OA | >20 |
| C14 | 58/37/5 IOA/VoAc/PSMac | 1.02 | none | 0.46 |
| 203 | 58/37/5 IOA/VoAc/PSMac | 0.89 | 20% IPM | 2.3 |
| 204 | 58/37/5 IOA/VoAc/PSMac | 0.89 | 30% IPM | 17.7 |
| 205 | 58/37/5 IOA/VoAc/PSMac | 0.89 | 40% IPM | >20 |
| 206 | 58/37/5 IOA/VoAc/PSMac | 0.89 | 30% OA | 1.1 |
| 207 | 58/37/5 IOA/VoAc/PSMac | 0.89 | 40% OA | >20 |
| C15 | 58/37/5 IOA/VoAc/PSMac | 1.02 | none | 0.44 |
| 208 | 58/37/5 IOA/VoAc/PSMac | 1.02 | 20% IPM | 3.9 |
| 209 | 58/37/5 IOA/VoAc/PSMac | 1.02 | 30% IPM | 11.2 |
| 210 | 58/37/5 IOA/VoAc/PSMac | 1.02 | 40% IPM | >20 |
| 211 | 58/37/5 IOA/VoAc/PSMac | 1.02 | 30% OA | 1.6 |
| 212 | 58/37/5 IOA/VoAc/PSMac | 1.02 | 40% OA | >20 |
| C16 | 53/37/10 IOA/VoAc/PMMAMac | 0.815 | none | 0.15 |
| 213 | 53/37/10 IOA/VoAc/PMMAMac | 0.815 | 30% OA | 0.32 |
| C17 | 53/37/10 IOA/VoAc/PMMAMac | 0.92 | none | 0.16 |
| 214 | 53/37/10 IOA/VoAc/PMMAMac | 0.92 | 30% OA | 0.36 |
| C18 | 58/37/5 IOA/VoAc/PMMAMac | 1.05 | none | 0.4 |
| 215 | 58/37/5 IOA/VoAc/PMMAMac | 1.05 | 30% OA | 0.67 |
| 216 | 58/37/5 IOA/VoAc/PMNAMac | 1.05 | 30% IPM | 0.71 |
| C19 | 58/37/5 IOA/VoAc/PMMAMac | 1.15 | none | 0.37 |
| 217 | 58/37/5 IOA/VoAc/PMMAMac | 1.15 | 30% OA | 0.7 |
| 218 | 58/37/5 IOA/VoAc/PMMAMac | 1.15 | 30% IPM | 0.8 |

EXAMPLE 219

Copolymer (58/37/5 IOA/VoAc/PSMac, 34 percent solids in 84/16 ethyl acetate/toluene, iv=0.89 dl/g) was knife coated at a wet thickness of about 7 mil (178 μM) onto a 2 mil (51 μM) polyethylene terephthalate film. The coated film was oven dried at 160° F. (71° C.) for 20 minutes and then at 210° F. (99° C.) for 10 minutes. Patches (5 cm$^2$ circles) each containing 0.044 g of dry adhesive were cut from the adhesive coated film. Nicotine (0.011 g) was placed on top of the adhesive in each patch using a micropipette to provide a patch with an adhesive layer containing 20 percent by weight of nicotine. The adhesive layer was covered with a release liner (SCOTCHPAK™ 1022) and allowed to equilibrate overnight. The rate of release of nicotine from the patch was determined using the test method described below. The results are shown in Table 7 below where each entry is the average of three independent determinations.

EXAMPLE 220

The method of Example 219 was repeated using a 58/37/5 IOA/VoAc/PSMac having an iv=1.02 dl/g. The rate of release of nicotine from the patch was determined using the test method described below. The results are shown in Table 7 below where each entry is the average of three independent determinations.

In-vitro Release of Nicotine

This method describes the dissolution test procedure used to evaluate in-vitro release characteristics of nicotine transdermal delivery patches.

The method uses a Hanson Dissolution Apparatus with the dissolution media temperature set at 32° C.; the paddle speed set at 50 rpm; and the paddle height above the sample set at 25 mm.

Each patch (5 cm$^2$) is affixed with double sided adhesive tape to a separate stainless steel plate so that the release liner is facing upward (backing is in direct contact with the double sided tape). Each dissolution flask is charged with 500 mL 0.1 M phosphate buffer (pH 6.0) and the temperature of the buffer is allowed to equilibrate 32±0.5° C.

The release liner is removed from the patch and the mounted patch is placed in the dissolution flask. At 5, 10, 20, 30, 60, 90, 120, 240, 480 and 720 minutes, 4 mL samples are withdrawn and analyzed for nicotine content using uv sprectrophotometry with the wavelength set at 262 nm using a 1 cm flow through the spectrophotometer cell. The results are reported as the cumulative percent nicotine released.

TABLE 7

In-vitro Nicotine Release

| | Cumulative Percent Nicotine Released | |
|---|---|---|
| Time (minutes) | Example 219 | Example 220 |
| 0 | 0 | 0 |
| 5 | 36.7 | 38.4 |
| 10 | 44.2 | 46.6 |
| 20 | 55.8 | 60.3 |
| 30 | 65.9 | 68.7 |
| 60 | 77.5 | 80.0 |
| 90 | 80.5 | 84.6 |
| 120 | 84.9 | 87.2 |
| 240 | 87.6 | 89.3 |
| 480 | 88.5 | 90.4 |
| 720 | 89.8 | 90.9 |

EXAMPLE 221

Using the method of Example 219, patches having an adhesive layer containing 25 percent by weight of nicotine were prepared using a 53/37/10 IOA/VoAc/ELVACITE 1020 copolymer having an iv=0.92 dl/g. The adhesive layer of the patch had many air bubbles. The compliance was found to be 1.5×$10^{-5}$ cm$^2$/dyne (average of three independent determinations).

EXAMPLE 222

Using the method of Example 219, patches having an adhesive layer containing 25 percent by weight of nicotine were prepared using a 58/37/5 IOA/VoAc/ELVACITE 1020 copolymer having an iv=1.15 dl/g. The compliance was found to be 0.9×10⁻⁵ cm²/dyne (average of three independent determinations).

EXAMPLE 223

Propylene glycol (1.52 g), methyl laurate (2.54 g), glyceryl monolaurate (0.25 g), N,N-dimethyldodecylamine-N-oxide (0.15 g), dried copolymer (5.53 g of 55/40/5 IOA/HEA/PMMAMac, iv=0.45 dl/g prior to drying) and solvent (15 g of 95/5 w/w ethyl acetate/isopropanol) were combined and mixed to provide a homogeneous coating formulation. The formulation was coated at a wet thickness of 20 mil (508 μM) onto a silicone coated polyester release liner (Daubert PESTER). The coated release liner was oven dried for 4 minutes at 43° C., for 3 minutes at 85° C., and for 2 minutes at 107° C. The coated release liner was then laminated to the corona treated side of a clear 2 mil (51 μM) polypropylene film. Patches (circular, 5 cm²) were die cut from the resulting laminate. One patch was applied to the left forearm of a human subject. A second patch was applied to the right forearm of the same subject. The percent of patch surface adhering to skin was approximated by visual assessment through the clear backing. The results are shown in Table 8 below.

EXAMPLE 224–261

Using the general method of Example 223, a number of patches were prepared and the adhesion to skin evaluated in order to assess the effect of copolymer composition, copolymer inherent viscosity, wet coating thickness, softener composition and the amount of softener on adhesion to skin. The formulations (amounts are percent by weight) and adhesion evaluations are shown in Table 8 below wherein the absence of an entry indicates that the adhesion was not assessed at that time point, "OFF" means that the patch fell off by itself, and "R" means that the patch was removed by the subject. All adhesion testing was conducted on the same subject and unless otherwise indicated the patch was adhered to the left forearm.

TABLE 8

| Example Number | Copolymer Type | iv (dl/g) | Softener | Wet Coating Thickness (mil/μM) | Adhesion (%) Day 0 | Day 1 | Day 2 | Day 3 | Day 4 |
|---|---|---|---|---|---|---|---|---|---|
| 223[1] | 55/40/5 IOA/HEA/PMMAMac | 0.45 | 15.2 PG; 25.4 ML; 2.5 GML | 20/508 | 100 | | 85 | 65 | 20 |
| 224[1,2] | 55/40/5 IOA/HEA/PMMAMac | 0.45 | 15.2 PG; 25.4 ML; 2.5 GML | 20/508 | 100 | | 95 | 85 | 50 |
| 225[1] | 55/40/5 IOA/HEA/PMMAMac | 0.45 | 10.1 PG; 30.5 ML; 2.5 GML | 20/508 | 100 | | 90 | 75 | 60 |
| 226[1,2] | 55/40/5 IOA/HEA/PMMAMac | 0.45 | 10.1 PG; 30.5 ML; 2.5 GML | 20/508 | 100 | | 95 | 85 | 50 |
| 227[1] | 55/40/5 IOA/HEA/PMMAMac | 0.45 | 5.1 PG; 35.5 ML; 2.5 GML | 20/508 | 100 | | 90 | 85 | 45 |
| 228[1,2] | 55/40/5 IOA/HEA/PMMAMac | 0.45 | 5.1 PG; 35.5 ML; 2.5 GML | 20/508 | 100 | | 90 | 75 | 25 |
| 229[1] | 60/35/5 IOA/HEA/PMMAMac | 0.75 | 15.2 PG; 25.4 ML; 2.5 GML | 20/508 | 100 | 95 | 65 | OFF | |
| 230[1,2] | 60/35/5 IOA/HEA/PMMAMac | 0.75 | 15.2 PG; 25.4 ML; 2.5 GML | 20/508 | 100 | 100 | 98 | 60 | R |
| 231[1] | 60/35/5 IOA/HEA/PMMAMac | 0.75 | 10.1 PG; 30.5 ML; 2.5 GML | 20/508 | 100 | 95 | 85 | 10 | R |
| 232[1,2] | 60/35/5 IOA/HEA/PMMAMac | 0.75 | 10.1 PG; 30.5 ML; 2.5 GML | 20/508 | 100 | 100 | 100 | ~98 | R |
| 233[1] | 60/35/5 IOA/HEA/PMMAMac | 0.75 | 5.1 PG; 35.5 ML; 2.5 GML | 20/508 | 100 | 95 | 10 | R | |
| 234[1,2] | 60/35/5 IOA/HEA/PMMAMac | 0.75 | 5.1 PG; 35.5 ML; 2.5 GML | 20/508 | 100 | 100 | 100 | ~95 | R |
| 235 | 55/40/5 IOA/HEA/PMMAMac | 0.45 | 30 OA | 15/381 | 100 | 95 | 80 | 60 | 50 |
| 236 | 55/40/5 IOA/HEA/PMMAMac | 0.45 | 44 OA | 15/381 | 100 | 85 | 70 | 65 | OFF |
| 237 | 55/40/5 IOA/HEA/PMMAMac | 0.45 | 30 ML | 15/381 | 100 | 50 | OFF | | |
| 238 | 55/40/5 IOA/HEA/PMMAMac | 0.45 | 44 ML | 15/381 | 100 | 90 | 65 | OFF | |
| 239[1] | 59/40/1 IOA/HEA/PMMAMaC* | 0.68 | 10.2 PG; 30.5 ML; 2.5 GML | 15/381 | 100 | 80 | 80 | 78 | 75 |
| 240[1] | 59/39/2 IOA/HEA/PMMAMaC* | 0.63 | 10.2 PG; 30.5 ML; 2.5 GML | 15/381 | 100 | 95 | ~93 | 90 | 80 |
| 241[1] | 58/39/3 IOA/HEA/PMMAMaC* | 0.62 | 10.2 PG; 30.5 ML; 2.5 GML | 15/381 | 100 | ~92 | ~88 | 40 | R |
| 242[1] | 58/38/4 IOA/HEA/PMMAMaC* | 0.69 | 10.2 PG; 30.5 ML; 2.5 GML | 15/381 | 100 | 85 | 75 | 40 | R |
| 243[1] | 59/40/1 IOA/HEA/PMMAMaC* | 0.68 | 10.2 PG; 30.5 ML; 2.5 GML | 25/635 | 100 | 90 | 80 | 75 | 70 |
| 244[1] | 59/39/2 IOA/HEA/PMMAMaC* | 0.63 | 10.2 PG; 30.5 ML; 2.5 GML | 25/635 | 100 | 100 | 100 | 100 | 95 |
| 245[1] | 58/39/3 IOA/HEA/PMMAMaC* | 0.62 | 10.2 PG; 30.5 ML; 2.5 GML | 25/635 | 100 | 100 | 90 | ~88 | 80 |
| 246[1] | 58/38/4 IOA/HEA/PMMAMaC* | 0.69 | 10.2 PG; 30.5 ML; 2.5 GML | 25/635 | 100 | ~98 | ~96 | 95 | 60 |
| 247[1] | 57/38/5 IOA/HEA/PSMac | 0.55 | 10.2 PG; 30.5 ML; 2.5 GML | 15/381 | 80 | 65 | 65 | OFF | |
| 248[1] | 57/38/5 IOA/HEA/PSMac | 0.32 | 10.2 PG; 30.5 ML; 2.5 GML | 15/381 | 95 | 85 | 80 | 75 | R |
| 249 | 57/38/5 IOA/HEA/PSMac | 0.55 | 44 EO | 15/381 | 100 | 85 | 70 | 60 | R |
| 250 | 57/38/5 IOA/HEA/PSMac | 0.55 | 44 OA | 15/381 | 95 | 70 | 20 | OFF | |
| 251 | 57/38/5 IOA/HEA/PSMac | 0.55 | 44 ML | 15/381 | 95 | 75 | 55 | 50 | R |
| 252 | 57/38/5 IOA/HEA/PSMac | 0.55 | 30 EO | 20/508 | 100 | 95 | 80 | 75 | R |
| 253 | 57/38/5 IOA/HEA/PSMac | 0.55 | 30 OA | 20/508 | 100 | OFF | | | |
| 254 | 57/38/5 IOA/HEA/PSMac | 0.55 | 30 ML | 20/508 | 100 | 30 | R | | |
| 255 | 57/38/5 IOA/HEA/PSMac | 0.55 | 30 IPM | 20/508 | 100 | ~98 | ~95 | ~93 | OFF |
| 256 | 57/38/5 IOA/HEA/PSMac | 0.55 | 44 EO | 20/508 | 100 | OFF | | | |
| 257 | 57/38/5 IOA/HEA/PSMac | 0.55 | 44 OA | 20/508 | 100 | OFF | | | |
| 258 | 57/38/5 IOA/HEA/PSMac | 0.55 | 44 ML | 20/508 | 100 | 50 | 35 | 35 | OFF |
| 259 | 57/38/5 IOA/HEA/PSMac | 0.55 | 44 IPM | 20/508 | 100 | 80 | 70 | 50 | OFF |
| 260[1] | 57/38/5 IOA/HEA/PSMac | 0.32 | 10.2 PG; 30.5 ML; 2.5 GML | 20/508 | 100 | 70 | 45 | 45 | OFF |
| 261[1] | 57/38/5 IOA/HEA/PSMac | 0.55 | 10.2 PG; 30.5 ML; 2.5 GML | 20/508 | 100 | 80 | 80 | OFF | OFF |

*PMMAac is ELVACITE 1020
[1]Formulation also contained 1.5% DDAO
[2]Adhesion test conducted on subject's right arm

What is claimed is:
1. A transdermal drug delivery device, comprising:
(1) a backing;
(2) a matrix adhered to one side of the backing and comprising
  (a) a copolymer comprising
    (i) one or more A monomers selected from the group consisting of alkyl acrylates containing 4 to 10 carbon atoms in the alkyl group and alkyl methacrylates containing 4 to 10 carbon atoms in the alkyl group; and
    (ii) optionally one or more ethylenically unsaturated B monomers copolymerizable with the A monomer; and
    (iii) a macromonomer comprising an ethylenically unsaturated group copolymerizable with the A and B monomers defined above and having a molecular weight in the range 500–500,000;
(b) a softener dissolved in the copolymer; and,
(c) if the softener is not therapeutically effective, a therapeutically effective amount of a drug,
    wherein the structure and amount of the comonomers in the copolymer, the inherent viscosity of the copolymer, and the amount and structure of the drug and the softener are such as to provide the matrix with a compliance value in the range of about $2 \times 10^{-6}$ cm$^2$/dyne to about $4 \times 10^{-3}$ cm$^2$/dyne.

2. A transdermal drug delivery device according to claim 1, wherein the B monomer or monomers comprises a functional group selected from the group consisting of carboxylic acid, carboxylic acid ester, hydroxy, sulfonamide, urea, carbamate, carboxamide, amine, oxy, oxo, and cyano.

3. A transdermal drug delivery device according to claim 1, wherein the B monomer or monomers are selected from the group consisting of acrylic acid, methacrylic acid, maleic acid, a hydroxyalkyl acrylate containing 2 to 4 carbon atoms in the hydroxyalkyl group, a hydroxyalkyl methacrylate containing 2 to 4 carbon atoms in the hydroxyalkyl group, acrylamide, methacrylamide, an alkyl substituted acrylamide containing 1 to 8 carbon atoms in the alkyl group, diacetone acrylamide, a dialkyl acrylamide having 1 or 2 carbon atoms in the alkyl group, N-vinyl-N-methyl acetamide, N-vinyl valerolactam, N-vinyl caprolactam, N-vinyl-2-pyrrolidone, glycidyl methacrylate, alkoxyethyl acrylate containing 1 to 4 carbon atoms in the alkoxy group, alkoxyethyl methacrylate containing 1 to 4 carbon atoms in the alkoxy group, 2-ethoxyethoxyethyl acrylate, furfuryl methacrylate, furfuryl acrylate, tetrahydrofurfuryl acrylate, tetrahydrofurfuryl methacrylate, propylene glycol monomethacrylate, propylene glycol monoacrylate, polyethylene glycol acrylate, polyethylene glycol methacrylate, polyethylene glycol methyl ether acrylate, polyethylene oxide methyl ether acrylate, di(lower)alkylamino ethyl acrylate, di(lower)alkylamino ethyl methacrylate, di(lower)alkylaminopropyl methacrylamide, acrylonitrile, methacrylonitrile, and vinyl acetate.

4. A transdermal drug delivery device according to claim 1, wherein the A monomer is present in an amount of about 40 to about 95 percent by weight, based on the total weight of all monomers in the copolymer.

5. A transdermal drug delivery device according to claim 1, wherein the A monomer is present in an amount of about 50 to about 70 percent by weight, based on the total weight of all monomers in the copolymer.

6. A transdermal drug delivery device according to claim 1, wherein the A monomer is selected from the group consisting of isooctyl acrylate, 2-ethylhexyl acrylate, butyl acrylate, and cyclohexyl acrylate.

7. A transdermal drug delivery device according to claim 1, wherein the B monomer is present in an amount from 0 to 60 percent by weight based on the total weight of the copolymer.

8. A transdermal drug delivery device according to claim 1, wherein the B monomer is present in an amount of greater than 25 percent by weight based on the total weight of the copolymer, to about 50 percent by weight based on the total weight of the copolymer.

9. A transdermal drug delivery device according to claim 1, wherein the B monomer is selected from the group consisting of hydroxyethyl acrylate, hydroxyethyl methacrylate, glyceryl acrylate, N,N-dimethyl acrylamide, 2-ethoxyethoxyethyl acrylate, 2-ethoxyethyl acrylate, tetrahydrofurfuryl acrylate, acrylic acid, acrylamide, and vinyl acetate.

10. A transdermal drug delivery device according to claim 1, wherein the macromonomer has a molecular weight in the range 5,000–30,000.

11. A transdermal drug delivery device according to claim 1, wherein the macromonomer is present in an amount of not more than about 15% by weight based on the total weight of all monomers in the copolymer.

12. A transdermal drug delivery device according to claim 1, wherein the macromonomer is present in an amount of not more than about 5% by weight based on the total weight of all monomers in the copolymer.

13. A transdermal drug delivery device according to claim 1, wherein the macromonomer is a compound of the formula

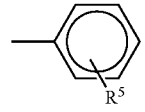

wherein X is a moiety comprising an ethylenically unsaturated group copolymerizable with the A and B monomers, $R^2$ is a hydrogen atom or a lower alkyl group, $R^3$ is a lower alkyl group or the residue of a free-radical initiator, n is an integer from 20 to 500 and each $R^4$ is a monovalent radical independently selected from the group consisting of —CN, and —CO$_2$R$^6$ wherein $R^5$ is a hydrogen atom or a lower alkyl group, and $R^6$ is a lower alkyl group.

14. A transdermal drug delivery device according to claim 1, wherein the macromonomer is selected from the group consisting of polymethylmethacrylate macromonomer, styrene/acrylonitrile macromonomer, and polystyrene macromonomer.

15. A transdermal drug delivery device according to claim 1, wherein the softener is present in an amount in excess of 20% and less than about 60% by weight based on the total weight of the matrix.

16. A transdermal drug delivery device according to claim 1, wherein the softener is selected from the group consisting of C$_8$–C$_{22}$ fatty acids, C$_8$–C$_{22}$ fatty alcohols, lower alkyl esters of C$_8$–C$_{22}$ fatty acids, monoglycerides of C$_8$–C$_{22}$ fatty acids, di(lower)alkyl esters of C$_6$–C$_8$ diacids, tetrahydrofuryl alcohol polyethylene glycol ether, polyethylene glycol, propylene glycol, ethoxyethoxy ethanol, diethylene glycol monomethyl ether, N,N-dimethyl dodecylamine-N-oxide, 2-(2-ethoxyethoxy)ethanol, and combinations of the foregoing.

17. A transdermal drug delivery device according to claim 1, wherein the softener is selected from the group consisting of dimethyl sulfoxide, glycerol, ethanol, ethyl acetate, acetoacetic ester, N-methyl pyrrolidone, isopropyl alcohol, alkylaryl ethers of polyethylene oxide, polyethylene oxide monomethyl ethers, and polyethylene oxide dimethyl ethers.

18. A transdermal drug delivery device according to claim 1, wherein the softener is selected from the group consisting of nicotine, nitroglycerine, chlorpheniramine, nicotinic acid benzyl ester, orphenadrine, scopolamine, and valproic acid.

19. A pressure sensitive skin adhesive comprising:
  (1) a copolymer comprising
    (a) one or more A monomers selected from the group consisting of alkyl acrylates containing 4 to 10 carbon atoms in the alkyl group and alkyl methacrylates containing 4 to 10 carbon atoms in the alkyl group; and
    (b) optionally one or more ethylenically unsaturated B monomers copolymerizable with the A monomer; and
    (c) a macromonomer comprising an ethylenically unsaturated group copolymerizable with the A and B monomers defined above and having a molecular weight in the range 500–500,000; and
  (2) a softener dissolved in the copolymer,
    wherein the structure and amount of the comonomers in the copolymer, the inherent viscosity of the copolymer, and the amount and structure of the softener are such as to provide the pressure sensitive sldn adhesive with a compliance value in the range $2\times10^{-6}$ cm$^2$/dyne to about $4\times10^{-3}$ cm$^2$/dyne.

20. A pressure sensitive skin adhesive according to claim 19, wherein the B monomer or monomers comprise a functional group selected from the group consisting of carboxylic acid, carboxylic acid ester, hydroxy, sulfonamide, urea, carbamate, carboxamide, amine, oxy, oxo, and cyano.

21. In a transdermal delivery system for administering at least one pharmacologically active agent comprising a flexible backing material impermeable to said active agent and an adhesive layer on said backing material, the improvement wherein said adhesive layer comprises a pressure sensitive adhesive composition comprised of (1) a percutaneous penetration enhancer to increase permeability of skin to transdermally administered pharmacologically active agents in admixture with (2) a macromer reinforced base polymer, said base polymer component comprising a phase separated graft copolymer comprised of copolymerized monomers A and B to form a backbone polymer having polymeric moieties grafted thereto, wherein monomer A is a monomeric acrylic or methacrylic ester of a non-tertiary alcohol having from 4 to 10 carbon atoms, and monomer B is a polar monomer which is copolymerizable with monomer A, said percutaneous penetration enhancer being present in said composition in an amount of up to 40 percent by weight based on the weight of the composition.

22. The delivery system of claim 21 wherein said graft polymeric moiety is a polymerized monoalkenyl-substituted aromatic hydrocarbon.

23. The delivery system of claim 22 wherein said polymerized monoalkenyl-substituted aromatic hydrocarbon comprises polystyrene.

24. The delivery system of claim 21 wherein the molecular weight of said graft polymeric moiety is in the range of from about 500 to 500,000.

25. The delivery system of claim 21 wherein said B monomer is selected from the group consisting of acrylic acid, methacrylic acid, acrylamide, methylacrylamide, acrylonitrile and methacrylonitrile.

26. The delivery system of claim 21 wherein said base polymer comprises from about 40 to 95 percent by weight of said A monomer.

27. The delivery system of claim 26 wherein said base polymer comprises from about 50 to 70 percent by weight of said A monomer.

28. The delivery system of claim 21 wherein said graft polymeric moiety comprises poly-alpha-methylstyrene.

29. The delivery system of claim 21 wherein said percutaneous penetration enhancer is present in said composition in an amount in the range of from 5 to 30 percent by weight.

30. A transdermal drug delivery device, comprising:
  (1) a backing;
  (2) a matrix adhered to one side of the backing and comprising
    (a) a copolymer comprising
      (i) one or more A monomers selected from the group consisting of alkyl acrylates containing 4 to 10 carbon atoms in the alkyl group and alkyl methacrylates containing 4 to 10 carbon atoms in the alkyl group; and
      (ii) optionally one or more ethylenically unsaturated B monomers copolymerizable with the A monomer; and
      (iii) a macromonomer comprising an ethylenically unsaturated group copolymerizable with the A and B monomers defined above; and
  (3) a skin penetration enhancer dissolved in the copolymer.

31. A pressure sensitive skin adhesive comprising:
  (1) a copolymer comprising
    (a) one or more A monomers selected from the group consisting of alkyl acrylates containing 4 to 10 carbon atoms in the alkyl group and alkyl methacrylates containing 4 to 10 carbon atoms in the alkyl group; and
    (b) optionally one or more ethylenically unsaturated B monomers copolymerizable with the A monomer; and
    (c) a macromonomer comprising an ethylenically unsaturated group copolymerizable with the A and B monomers defined above; and
  (2) a skin penetration enhancer dissolved in the copolymer.

32. A transdermal drug delivery device, comprising:
  (1) a backing;
  (2) a matrix adhered to one side of the backing and comprising
    (a) a copolymer comprising
      (i) one or more A monomers selected from the group consisting of alkyl acrylates containing 4 to 10 carbon atoms in the alkyl group and alkyl methacrylates containing 4 to 10 carbon atoms in the alkyl group; and
      (ii) optionally one or more ethylenically unsaturated B monomers copolymerizable with the A monomer; and
      (iii) a macromonomer comprising an ethylenically unsaturated group copolymerizable with the A and B monomers defined above; and
  (3) a softener dissolved in the copolymer,
    wherein the structure and amount of the comonomers in the copolymer, the inherent viscosity of the copolymer, and the amount and structure of the softener are such as to provide the pressure sensitive skin adhesive with a compliance value in the range $2\times10^{-6}$ cm$^2$/dyne to about $1\times10^{-3}$ cm$^2$/dyne.

33. The transdermal drug delivery device of claim 1 wherein the softener is selected from the group consisting of nicotine, nitroglycerine, chlorpheniramine, nicotinic acid benzyl ester, orphenadrine, scopolamine, valproic acid and mixtures thereof.

34. The transdermal drug delivery device of claim 32 wherein the softener is selected front the group consisting of nicotine, nitroglycerine, chlorpheniramine, nicotinic acid benzyl ester, orphenadrine, scopolamine, valproic acid and mixtures there.

* * * * *

UNITED STATES PATENT AND TRADEMARK OFFICE
CERTIFICATE OF CORRECTION

PATENT NO. : 7,097,853 B1
APPLICATION NO. : 08/968519
DATED : August 29, 2006
INVENTOR(S) : James E. Garbe It is certified that error appears in the above-identified patent and that said Letters Patent is hereby corrected as shown below:

Title Page
Other Publications, Line 50, Delete "Functionality" and insert in place thereof -- Functionally -- ;

Title Page 3
Column 2, Line 25, Delete "Dependant" and insert in place thereof -- Defendant -- ;

Title Page 3
Column 1, Line 9, Insert the word -- by -- in between the words "Submission" and "Adhesives";

Title Page 3
Column 1, Line 24, Delete "Join" and insert in place thereof -- Joint -- ;

Title Page 3
Column 1, Line 5, Delete "Dependant" and insert in place thereof -- Defendant -- ;

Column 3
Line 9, Delete "isobomyl" and insert in place thereof -- isobornyl -- ;

Column 3
Line 35, Delete "furfryl" and insert in place thereof -- furfuryl -- ;

Column 3
Line 36, Delete "furfryl" and insert in place thereof -- furfuryl -- ;

Column 3
Line 37, Delete "tetrahydrofurfryl" and insert in place thereof -- tetrahydrofurfuryl -- ;

Column 6
Line 43, Delete "$5 \times 10^{314}$" and insert in place thereof -- $5 \times 10^{-4}$ -- ;

Column 8
Line 37, after "Krampe" delete "at" and insert in place thereof -- et -- ;

Column 10
Line 54, Delete "(1L/rnin)" and insert in place thereof -- (1L/min) -- ;

Column 13
Line 65-66, Delete "macromononier" and insert in place thereof -- macromonomer -- ;

UNITED STATES PATENT AND TRADEMARK OFFICE
CERTIFICATE OF CORRECTION

PATENT NO. : 7,097,853 B1
APPLICATION NO. : 08/968519
DATED : August 29, 2006
INVENTOR(S) : James E. Garbe It is certified that error appears in the above-identified patent and that said Letters Patent is hereby corrected as shown below:

Column 14
Line 17, Delete "solvvent" and insert in place thereof -- solvent -- ;

Column 14
Line 18, Delete "monmers." and insert in place thereof -- monomers. -- ;

Column 17-18, Table 3
Example Number 80, Delete "LPM" and insert in please thereof -- IPM --;

Column 17-18, Table 3
Example Number 81, delete "5I/34/15" and insert in place thereof -- 51/34/15 -- ;

Column 17-18, Table 3
Example Number 81, Delete "LPM" and insert in place thereof -- IPM -- ;

Column 17-18, Table 3
Example Number 83, Delete "IOA/HEAIPMMAMac*" and insert in place thereof -- IOA/HEA/PMMAMac* -- ;

Column 17-18, Table 3
Example Number 87, Delete "IOA/HEAIPMMAMac*" and insert in place thereof -- IOA/HEA/PMMAMac* -- ;

Column 17-18, Table 3
Example Number 89, Delete "IOA/HEAIPMMAMac*" and insert in place thereof -- IOA/HEA/PMMAMac* -- ;

Column 19-20, Table 3
Example Number 92, Delete "IOA/HEAIPSMac*" and insert in place thereof -- IOA/HEA/PSMac* -- ;

Column 19-20, Table 4
Line 40, Insert -- ) -- after "$cm^2/dyne$" ;

Column 19-20, Table 4
Example Number 111, Delete "IOAIHEA/PMMAMac*" and insert in place thereof -- IOA/HEA/PMMAMac* -- ;

Column 19-20, Table 4
Example Number 114, Delete "54/36/IO" and insert in place thereof -- 54/36/10 -- ;

UNITED STATES PATENT AND TRADEMARK OFFICE
CERTIFICATE OF CORRECTION

PATENT NO. : 7,097,853 B1
APPLICATION NO. : 08/968519
DATED : August 29, 2006
INVENTOR(S) : James E. Garbe It is certified that error appears in the above-identified patent and that said Letters Patent is hereby corrected as shown below:

Column 19-20, Table 4
Example Number 123, Delete "57/3815" and insert in place thereof -- 57/38/15 -- ;

Column 19-20, Table 4
Example Number 123, Delete "IOA/HEAIPMMAMac*" and insert in place thereof -- IOA/HEA/PMMAMac* -- ;

Column 19-20, Table 4
Example Number 126, Delete "IOAIHEA/PMMAMac*" and insert in place thereof -- IOA/HEA/PMMAMac* -- ;

Column 19-20, Table 4
Example Number 127, Delete "IOAIHEA/PMMAMac*" and insert in place thereof -- IOA/HEA/PMMAMac* -- ;

Column 21
Line 3, Delete "IOA/IDMACM/" and insert in place thereof -- IOA/DMACM/ -- ;

Column 21
Line 12, After "2" delete "mi" and insert in place thereof -- minutes at -- ;

Column 23-24, Table 5
Ex No. 164, Delete "6O/15/15/10" and insert in place thereof -- 60/15/15/10 -- ;

Column 23-24, Table 5
Ex No. 174, Delete "1.0" and insert in place thereof -- 1.1 -- ;

Column 23-24, Table 5
Ex No. 177, Delete "7.3 DIPA" and insert in place thereof -- 7.7 DIPA -- ;

Column 26
Line 45, Delete "tetrahydrofrfurly" and insert in place thereof -- tetrahydrofurfuryl -- ;

Column 26
Line 61, Delete "(381 ∞M)" and insert in place thereof -- (381 µM) -- ;

Column 28
Line 27, Delete "IOA/IVoAc/PSMac," and insert in place thereof -- IOA/VoAc/PSMac, -- ;

UNITED STATES PATENT AND TRADEMARK OFFICE
CERTIFICATE OF CORRECTION

PATENT NO. : 7,097,853 B1
APPLICATION NO. : 08/968519
DATED : August 29, 2006
INVENTOR(S) : James E. Garbe It is certified that error appears in the above-identified patent and that said Letters Patent is hereby corrected as shown below:

Column 28
Line 43, Delete "EXAMPLE" and insert in place thereof -- EXAMPLES --;

Columns 27-28
Table 6, Line 57, Delete "cm/$^2$/dyne" and insert in place thereof -- cm$^2$/dyne--;

Columns 27-28
Table 6, Example Number C13, Delete "0.87" and insert in place thereof -- 1.02 --;

Columns 29-30
Table 6, Line 5, Delete "cm/$^2$/dyne" and insert in place thereof -- cm$^2$/dyne -- ;

Columns 29-30
Table 6, Example Number C14, Delete "1.02" and insert in place thereof -- 0.89 --;

Columns 29-30
Table 6, Example Number C16, Delete "IOA/VoAc/PMNAMac" and insert in place thereof -- IOA/VoAc/PMMAMac -- ;

Column 29
Line 67, After the word "equilibrate" insert the word -- at -- ;

Column 30
Lines 31-32, Delete "sprectrophotometry" and insert in place thereof
-- spectrophotmetry -- ;

Columns 31-32
Example Number 239[1], "IOA/HEA/PMMAMaC*" and insert in place thereof
-- IOA/HEA/PMMAMac* -- ;

Columns 31-32
Example Number 240[1], "IOA/HEA/PMMAMaC*" and insert in place thereof
-- IOA/HEA/PMMAMac* -- ;

Columns 31-32
Example Number 241[1], "IOA/HEA/PMMAMaC*" and insert in place thereof
-- IOA/HEA/PMMAMac* -- ;

Columns 31-32
Example Number 242[1], "IOA/HEA/PMMAMaC*" and insert in place thereof
-- IOA/HEA/PMMAMac* -- ;

UNITED STATES PATENT AND TRADEMARK OFFICE
CERTIFICATE OF CORRECTION

PATENT NO. : 7,097,853 B1
APPLICATION NO. : 08/968519
DATED : August 29, 2006
INVENTOR(S) : James E. Garbe It is certified that error appears in the above-identified patent and that said Letters Patent is hereby corrected as shown below:

Columns 31-32
Example Number 243[1], "IOA/HEA/PMMAMaC*" and insert in place thereof
-- IOA/HEA/PMMAMac* -- ;

Columns 31-32
Example Number 245[1], "IOA/HEA/PMMAMaC*" and insert in place thereof
-- IOA/HEA/PMMAMac* -- ;

Columns 31-32
Example Number 246[1], "IOA/HEA/PMMAMaC*" and insert in place thereof
-- IOA/HEA/PMMAMac*" -- ; .

Columns 31-32
Below Table 8, Delete "*PMMAac" and insert in place thereof -- PMMAMac -- ;

Column 32
Line 1, Delete "EXAMPLE" and insert in place thereof -- EXAMPLES -- ;

Signed and Sealed this

Twenty-fourth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,097,853 B1
APPLICATION NO. : 08/968519
DATED : August 29, 2006
INVENTOR(S) : James E. Garbe et al.

Page 1 of 1

It is certified that error appears in the above-identified patent and that said Letters Patent is hereby corrected as shown below:

In claim 1, column 33, line 8, "with the A" should read --with A--.

In claim 1, column 33, line 11, "and," should read --and--.

In claim 16, column 34, lines 58-59, "tetrahydrofuryl," should read --tetrahydrofurfuryl,--.

In claim 21, column 35, line 33, "atransdermal" should read --a transdermal--.

In claim 31, column 36, line 27, after "skin adhesive", insert --for use in a transdermal drug delivery system--.

In claim 31, column 36, line 40, after "above;", delete "and".

In claim 31, column 36, lines 41-42, after "copolymer", insert --; and (3) a therapeutically effective amount of a drug--.

In claim 34, column 37, line 5, "front" should read --from--.

In claim 34, column 38, line 3, "there" should read --thereof--.

Signed and Sealed this

Eleventh Day of March, 2008

JON W. DUDAS
*Director of the United States Patent and Trademark Office*

UNITED STATES PATENT AND TRADEMARK OFFICE
CERTIFICATE OF CORRECTION

PATENT NO. : 7,097,853 B1
APPLICATION NO. : 08/968519
DATED : August 29, 2006
INVENTOR(S) : James E. Garbe et al.

It is certified that error appears in the above-identified patent and that said Letters Patent is hereby corrected as shown below:

In claim 1, column 33, lines 13-19, after "drug", delete ", wherein the structure and amount of the comonomers in the copolymer, the inherent viscosity of the copolymer, and the amount and structure of the drug and the softener are such as to provide the matrix with a compliance value in the range of about $2 \times 10^{-6}$ cm$^2$/dyne to about $4 \times 10^{-3}$ cm$^2$/dyne".

In claim 19, column 35, line 7, after "A pressure sensitive skin adhesive" insert --for use in a transdermal drug delivery system--.

In claim 19, column 35, line 19, after "500-500,000;" delete "and".

In claim 19, column 35, lines 20-26, after "copolymer", delete ", wherein the structure and amount of the comonomers in the copolymer, the inherent viscosity of the copolymer, and the amount and structure of the softener are such as to provide the pressure senitive sldn adhesive with a compliance value in the range $2 \times 10^{-6}$ cm$^2$/dyne to about $4 \times 10^{-3}$ cm$^2$/dyne".

In claim 19, column 35, line 20, after "copolymer" insert --and (3) if the softener is not therapeutically effective, a therapeutically effective amount of a drug--.

In claim 31, column 36, line 27, after "A pressure sensitive skin adhesive" insert --for use in a transdermal drug delivery system--.

In claim 31, column 36, line 39, after "monomers defined above;" delete "and".

UNITED STATES PATENT AND TRADEMARK OFFICE
CERTIFICATE OF CORRECTION

PATENT NO. : 7,097,853 B1
APPLICATION NO. : 08/968519
DATED : August 29, 2006
INVENTOR(S) : James E. Garbe et al.

It is certified that error appears in the above-identified patent and that said Letters Patent is hereby corrected as shown below:

In claim 31, column 36, lines 41-42, after "copolymer" insert --and (3) a therapeutically effective amount of a drug--.

In claim 32, column 36, lines 59-65, after "copolymer", delete ", wherein the structure and amount of the comonomers in the copolymer, the inherent viscosity of the copolymer, and the amount and structure of the softener are such as to provide the pressure sensitive skin adhesive with a compliance value in the range $2 \times 10^{-6}$ cm$^2$/dyne to about $1 \times 10^{-3}$ cm$^2$/dyne".

Signed and Sealed this

First Day of September, 2009

David J. Kappos
*Director of the United States Patent and Trademark Office*